United States Patent
Gaffney et al.

(10) Patent No.: US 6,291,660 B1
(45) Date of Patent: Sep. 18, 2001

(54) FUNGAL GENES REQUIRED FOR NORMAL GROWTH AND DEVELOPMENT

(75) Inventors: Thomas Deane Gaffney, Chapel Hill, NC (US); Juergen Wendland, Lörrach (DE); Fred Dietrich, Basel; Peter Philippsen, Riehen, both of (CH); Stephen Arthur Goff, Encinitas, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/415,522

(22) Filed: Oct. 8, 1999

Related U.S. Application Data

(60) Provisional application No. 60/172,224, filed on Oct. 8, 1998.

(51) Int. Cl.$^7$ .................................................. C07H 21/04
(52) U.S. Cl. ............................................................. 536/23.1
(58) Field of Search ............................................. 536/23.1

(56) References Cited

U.S. PATENT DOCUMENTS 5,821,090   10/1998   Revuelta Doval et al. .

FOREIGN PATENT DOCUMENTS 0 866 129 A2   9/1998   (EP) .
WO 93/04180    3/1993   (WO) .

OTHER PUBLICATIONS

Whiteway et al. Dominant negative selection of heterologous genes: Isolation of Candida albicans genes that interfere with *Saccharomyces cerevisiae* mating factor–induced cel cycle arrest. PNAS vol. 89:9410–9414, Nov. 1992.*
Qaife et al. INduction of a new metallothionein isoform (MT–IV) occurs during differentiation of stratified squamous epithelia. Biochemistry vol. 33:7250–7259, Jul. 1994.*
Matsui et al., Gene, 114: 43–49 (1992).
Altmann–Johl et al., Molecular Gene. Genet. 250: 69–80 (1996).
Madaule et al., Proc. Natl. Acad. Sci., 84: 779–783 (1987).
Bundock et al., The EMBO Journal 14(13): 3206–3214 (1995).
Matsui et al. Mol. Cell Biol., 12:5690–9 (1992).
Imai et al., Genetics, 142: 359–69 (1996).
Zheng et al., J. Biol. Chem., 268, No. 33: 24629–24634 (1993).
Healy et a., Mol. Cell Biol., 11, No. 11: 5767–5780 (1991).
Bender et al., Mol. Cell Biol., 11, No. 3: 1295–1305 (1991).
Zheng et al., J. Biol Chem., 269:2369–2372 (1994).
Chan et al., Genetics, 135: 677–691 (1993).
Lamarche et al., Trends Genet., 10, No. 12: 436–440 (1994).
Stevenson et al., Genes Dev., 9: 2949–2963 (1995).
Gibson et al., Trends Biochem. Sci., 19:349–353 (1994).
Chant et al., Cell 65: 1203–1212 (1991).
Chant et al., J. Cell Biol., 129: 767–78 (1995).
Sanders et al., Curr. Biol., 5, No. 11: 1213–1215 (1995).
Yang et al., J. Cell Biol., 136, No. 1: 111–123 (1997).
Dorer et al., Genetics, 146: 39–55 (1997).
Ohya et al., Mol. Biol. Cell, 4: 1017–1025 (1993).
Yamochi et al., J. Cell Biol., 25, No. 5: 1077–1093 (1994).
Qadota et al., Proc. Natl. Acad. Sci. USA, 91: 9317–9321 (1994).
Cid et al., Microbiology, 144: 25–36 (1998).
Cid et al., Microbiol. Rev., 59: 345–386 (1995).
Qadota et al., Science, 272:279–281 (1996).
Drgonova et al., Science 272: 277–279 (1996).
Kamada et al., J. Biol. Chem., 271, No. 16: 9193–9196 (1996).
Ozaki et al., EMBO J., 15, No. 9: 2196–2207 (1996).
Mazur et al., J. Biol. Chem., 271, No. 24: 14604–9 (1996).
Chen et al., Mol. Cell Biol. 16: 1376–1390 (1996).
Clemens et al., Mol. Cell Biol., 16, No. 9: 4656–4664 (1996).
Nonaka et al., EMBO J., 14, No. 23: 5931–5938 (1995).
Schmidt et al., Cell, 88: 531–542 (1997).
Imamura et al., EMBO J., 16, No. 10: 2745–2755 (1997).
Sasamura et al., Mol. Gen. Genet., 254: 486–494 (1997).
Kondoh et al., J. Bacteriol., 179, No. 24: 7734–7741 (1997).
Alberts et al., J. Biol. Chem., 273, No. 15:8616–8622 (1998).
Bickle et al., EMBO J., No. 8:2235–2245 (1998).
Fujiwara et al., Mol. Biol. Chem., 9: 1221–1233 (1998).
Chen et al., Genes & Development, 11:2958–2971 (1977).
Hermann et al., The Journal of Cell Biology, 137, No. 1: 141–153 (1997).
Hong et al., Molecular and Cellular Biology, 14, No. 2: 1017–1025 (1994).
Kim et al., The Journal of Cell Biology, 127, No. 5: 1381–1394 (1994).
Peterson et al., The Journal of Cell Biology, 127, No. 5: 1395–1406 (1994).
Smith et al., Science, 274: 2069–2074 (1996).
Wang et al., Genetics, 147: 1595–1607 (1997).
Wang et al., Molecular Biology of the Cell, 6: 1011–1024 (1995).

* cited by examiner

*Primary Examiner*—Terry McKelvey
*Assistant Examiner*—William Sandals
(74) *Attorney, Agent, or Firm*—Bruce Vrana

(57) ABSTRACT

The present invention relates to genomic DNA sequences obtained from terminal sequencing of random genomic fragments of the filamentous fungus *Ashbya gossypii*, to the sequences obtained therewith and the use of the sequences for forensic identification, to characterize genes and gene organization or this ascomycete by inter-genomic comparison, to identify biosynthetic genes that can be used as selection markers, to isolate promoters and terminators for application in a homologous as well as heterologous context, to find putative centromere containing clones, chromosome mapping, chromosome identifying, general information about chromosome organization and in addition to identify ORF containing SRS sequences with no homology to *S. cervisiae* or any other organism which allows the identification of *A. gossypii* specific genes.

6 Claims, No Drawings

FUNGAL GENES REQUIRED FOR NORMAL GROWTH AND DEVELOPMENT

This application claims the benefit of U.S. Provisional Application No. 60/172,224, filed Oct. 8, 1998. The disclosure of this priority document is hereby expressly incorporated by reference in its entirety into the instant disclosure.

FIELD OF THE INVENTION

The invention relates to nucleic acid sequences isolated from *Ashbya gossypii* that encode proteins essential for fungal growth. The invention also includes the methods of using these proteins pesticide targets, particularly fungicide targets, based on the essentiality of the gene for normal growth and development. The invention is also useful as a screening assay to identify inhibitors that are potential pesticides, particularly fungicides.

BACKGROUND OF THE INVENTION

The phytopathogenic fungus *Ashbya gossypii* is a filamentously growing ascomycete that was first isolated as a plant pathogen in tropical and sub-tropical regions. It infects the seed capsule of cotton plants and has also been isolated from tomatoes and citrus fruits. The infection of the seed capsule is caused by transmission of *A. gossypii* mycelium pieces or spores by stinging-sucking insects and causes a disease called stigmatomycosis. Presently, *A. gossypii* represents the most compact eukaryotic genome, compared to genome sizes of 12.5 Mb for *S. cerevisiae* (Chu et al., 1986), 31.0 Mb for *Aspergillus nidulans* (Brody and Carbon, 1989) and 47.0 Mb for *Neurospora crassa* (Orbach et al., 1988).

*A. gossypii* is systematically grouped to the endomycetales belonging to the family of spermophthoraceae. This classification is based on the observation that the spores that develop in hyphal compartments called sporangia look like ascospores, which are defined as endproducts of meiosis.

Since *Ashbya gossypii* is a filamentous ascomycete, and is capable of growing only by filamentous (hyphal) growth, fungal targets found in this model organism are predictive of targets which will be found in other pathogens, the vast majority of which grow in a filamentous fashion.

SUMMARY OF THE INVENTION

It is an object of the invention to provide an effective and beneficial method to identify novel pesticides, particularly fungicides. A feature of the invention is the identification of genes having a putative activity based on their homology to yeast genes. Genes of the invention comprise a putative GTP binding protein genes (herein referred to as AG001 and AG002 genes), putative GTPase activating protein genes (AG003 and AG004), putative phosphatidylinositol-4 kinase protein gene (AG005) and putative cytokinesis gene (AG006). Another feature of the invention is the discovery that the genes of the invention, AG001 (SEQ ID. NO: 1), AG002 (SEQ Id. NO 3):, AG003 (SEQ ID. NO: 5), AG004 (SEQ ID. NO: 7), AG005 (SEQ Id. NO: 9) and AG006(SEQ ID. NO: 11) are essential for fungal growth and development. An advantage of the present invention is that the newly discovered essential genes containing a novel fungicidal mode of action enables one skilled in the art to easily and rapidly identify novel fungicides.

One object of the present invention is to provide essential genes in fungi for assay development to detect inhibitory compounds with pesticidal, particularly fungicidal activity. Genetic results show that when AG001, AG002, AG003, AG004, AG005 and AG006 are mutated in *Ashbya gossypii*, the resulting phenotype is at best suppressed growth and at worst lethal. Suppressed growth as used herein results in a growth rate of half the growth rate observed in wild type or lower where 10% that of the wild-type growth rate was observed or no growth was macroscopically detected at all. Applicants further observed that when AG001, AG002, AG003, AG004, AG005 and AG006 are mutated in *Ashbya gossypii* abnormal filament development was observed. This suggests a critical role for the gene products encoded by the mutated genes.

The inventors of the present invention have demonstrated that the gene products of the invention are essential in *Ashbya gossypii*. This implies that chemicals which inhibit the function of the protein in fungi, particularly, filamentous fungi, are likely to have detrimental effects on fungi and are potentially good fungicide candidates. The present invention therefore provides methods of using a purified protein encoded by the gene sequence described below to identify inhibitors thereof, which can then be used as fungicides to suppress the growth of pathogenic fungi.

Pathogenic fungi is defined as those capable of colonizing a host and causing disease. Examples of fungal pathogens include plant pathogens such as *Septoria tritici, Stagnospora nodorum, Botrytis cinerea, Fusarium graminearum, Magnaporthe grisea, Cochliobolus heterostrophus, Colletotrichum heterostrophus, Ustilago maydis, Erisyphe graminis*, plant pathogenic oomycetes such as *Pythium ultimum* and *Phytophthora infestans*, and human pathogens such as *Candida albicans* and *Aspergillus fumigatus*

The present invention discloses novel nucleotide sequences derived from *Ashbya gossypii* designated as the AG001 gene, the AG002 gene, the AG003 gene, the AG004 gene, the AG005 gene and the AG006 gene. The nucleotide sequence of the genomic clones are set forth in SEQ ID NO: 1, SEQ ID NO: 3, SEQ ID NO: 5, SEQ ID NO: 7, SEQ ID NO: 9 and SEQ ID NO: 11 respectively. The amino acid sequence encoded by the above sequences are set forth in SEQ ID NO: 2, SEQ ID NO:4, SEQ ID NO:6, SEQ ID NO: 8, SEQ ID NO:10 or SEQ ID NO:12 . The present invention also includes nucleotide sequences substantially similar to those set forth in SEQ ID NO: 1, SEQ ID NO: 3, SEQ ID NO: 5, SEQ ID NO: 7, SEQ ID NO: 9 OR SEQ ID NO: 11 and amino acid sequences substantially similar to those set out in SEQ ID NO: 2, SEQ ID NO:4, SEQ ID NO:6, SEQ ID NO: 8, SEQ ID NO:10 or SEQ ID NO:12

The present invention also encompasses fungal proteins whose amino acid sequence are substantially similar to the amino acid sequences set forth in SEQ ID NO: 2, SEQ ID NO:4, SEQ ID NO:6, SEQ ID NO: 8, SEQ ID NO:10 or SEQ ID NO:12. In a particular embodiment, the present invention encompasses nucleic acid sequences and amino acid sequences of filamentous fungi. The present invention also includes methods of using the AG001 to AG006 gene products as fungicide targets, based on the essentiality of the genes for normal growth and development. Normal growth and development is defined as a growth rate substantially similar to that observed in wild type fungus, preferably greater than at least 50% the growth rate observed in wild type fungus and particularly greater than 10% the growth rate obeserved in wild type fungus. Normal growth and development may also be defined, when used in relation to filamentous fungi, as normal filament development development (including normal septation and normal nuclear migration and distribution), normal sporulation, and normal production of any infection structures (e.g. appressoria). Conversely suppressed or inhibited growth as used herein is defined as less than half the growth rate observed in wild type or lower where 10% that of the wild-type growth rate was observed or no growth was macroscopically detected at all or abnormal filament development.

Furthermore, the invention can be used in screening assays to identify inhibitors that are potential pesticides, particularly fungicides. Encompassed by the present invention is the use of sequences selected from the attached Sequence Listing to identify substances having antifungal activity; the use of sequences selected from the attached Sequence Listing to identify substances having pesticidal, particularly fungicidal, activity.

Further comprised is the use of an a DNA sequence selected from the Sequence Listing and variants thereof in a screening method for identifying compounds capable of inducing broad spectrum disease resistance in plants.

In a further embodiment according to the invention, a DNA sequence selected from the Sequence Listing may also be used for distinguishing among different species of plant pathogenic fungi and for distinguishing fungal pathogens from other pathogens such as bacteria. In another preferred embodiment, the present invention describes a method for identifying chemicals having the ability to inhibit any one or more of AG001, AG002, AG003, AG004, AG005 and AG006 activity in fungi preferably comprising the steps of: a) obtaining transgenic fungus and/or fungal cell, preferably stably transformed, comprising a non-native nucleotide sequence or an endogenous nucleotide sequences operably linked to non-native promoter, preferably an inducible promoter, encoding an enzyme having and activity and capable of overexpressing an enzymatically active AG001, AG002, AG003, AG004, AG005 or AG006 gene product where overexpression of the gene product is suppresses or inhibits the normal growth and development of the fungus; b) applying a compound to the transgenic fungus and/or fungal cell c) determining the growth and/or development of the transgenic fungus and/or fungal cell after application of the compound; d) comparing the growth and/or development of the transgenic fungus and/or fungal cell after application of the chemical to the growth and/or development of the corresponding transgenic fungus and/or fungal cell to which the compound was not applied; and e) selecting compound that does not results in reduction of the suppressed or inhibited growth and/or development in the transgenic fungus and/or fungal cell in comparison to the untreated transgenic fungus and/or fungal cell.

In a preferred embodiment, the proteins having AG001, AG002, AG003, AG004, AG005 or AG006 activities are encoded by nucleotide sequence derived from fungi, preferably filamentous fungi, particularly from *Ashbya gossypii*, desirably identical or substantially similar to the nucleotide sequence set forth in SEQ ID NO:1, SEQ ID NO:3, SEQ ID NO:5, SEQ ID NO: 7, SEQ ID NO:9 or SEQ ID NO:11. In another embodiment, the proteins having AG001, AG002, AG003, AG004, AG005 or AG006 activity are encoded by nucleotide sequences capable of encoding the amino acid sequences of: SEQ ID NO: 2, SEQ ID NO:4, SEQ ID NO:6, SEQ ID NO: 8, SEQ ID NO:10 or SEQ ID NO:12. In yet another embodiment, the proteins having AG001, AG002, AG003, AG004, AG005 or AG006 activity have amino acid sequences identical or substantially similar to the amino acid sequence set forth in SEQ ID NO: 2, SEQ ID NO:4, SEQ ID NO:6, SEQ ID NO: 8, SEQ ID NO:10 or SEQ ID NO:12 respectively.

The invention also provides a method for suppressing the growth of a fungus comprising the step of applying to the fungus a compound that inhibits the naturally occurring AG001, AG002, AG003, AG004, AG005 and/or AG006 activity in the fungus.

Other objects and advantages of the present invention will become apparent to those skilled in the art from a study of the following description of the invention and non-limiting examples.

Definitions

For clarity, certain terms used in the specification are defined and presented as follows:

Co-factor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

Enzyme activity: means herein the ability of an enzyme to catalyze the conversion of a substrate into a product. A substrate for the enzyme comprises the natural substrate of the enzyme but also comprises analogues of the natural substrate which can also be converted by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Heterologous DNA Sequence: a DNA sequence not naturally associated with a host cell into which it is introduced, including non-naturally occurring multiple copies of a naturally occurring DNA sequence.

Homologous DNA Sequence: a DNA sequence naturally associated with a host cell into which it is introduced.

Isogenic: plants which are genetically identical, except that they may differ by the presence or absence of a transgene.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, a transgenic host cell.

Mature protein: protein which is normally targeted to a cellular organelle, such as a chloroplast, and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is larger than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M.S. Introduction to Computational Biology: Maps, sequences and genomes. Chapman & Hall. London: 1995. ISBN 0-412-99391-0). The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO4, 1 mM EDTA at 50° C. with washing in 2×SSC, 0.1% SDS at 50° C., more desirably in 7% sodium dodecyl sulfate (SDS), 0.5 M NaPO4, 1 mM EDTA at 50° C. with washing in 1×SSC, 0.1% SDS at 50° C., more desirably still in 7% sodium dodecyl sulfate (SDS), 0.5 M NaPO4, 1 MM EDTA at 50° C. with washing in 0.5×SSC, 0.1% SDS at 50° C., preferably in 7% sodium dodecyl sulfate (SDS), 0.5 M NaPO4, 1 mM EDTA at 50° C. with washing in 0.1×SSC, 0.1% SDS at 50° C., more preferably in 7% sodium dodecyl sulfate (SDS), 0.5 M NaPO4, 1 mM EDTA at 50° C. with washing in 0.1×SSC, 0.1% SDS at 65° C.

The term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 52%, more desirably 65%, more desirably at least 75%, preferably at least 85%, more preferably at least 90%, still more preferably at least 95%, yet still more preferably at least 99%.

Substrate: a substrate is the molecule that the enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Tolerance: the ability to continue normal growth or function when exposed to an inhibitor or herbicide in an amount sufficient to suppress the normal growth or function of native, unmodified plants.

Transformation: a process for introducing heterologous DNA into a cell, tissue, or plant. Transformed cells, tissues, or plants are understood to encompass not only the end product of a transformation process, but also transgenic progeny thereof.

Transgenic: stably transformed with a recombinant DNA molecule that preferably comprises a suitable promoter operatively linked to a DNA sequence of interest.

BRIEF DESCRIPTION OF THE SEQUENCES IN THE SEQUENCE LISTING

SEQ ID NO:1 comprises a AG001 coding region
SEQ ID NO:2 comprises an amino acid sequence encoded by the coding region of SEQ ID NO:1
SEQ ID NO:3 comprises a AG002coding region.
SEQ ID NO:4 comprises an amino acid sequence encoded by the coding region of SEQ ID NO:3.
SEQ ID NO:5 comprises a AG003 coding region.
SEQ ID NO:6 comprises an amino acid sequence encoded by the coding region of SEQ ID NO:5.
SEQ ID NO:7 comprises a AG004 coding region.
SEQ ID NO:8 comprises an amino acid sequence encoded by the coding region of SEQ ID NO:7.
SEQ ID NO:9 comprises a AG005 coding region.
SEQ ID NO:10 comprises an amino acid sequence encoded by coding region of SEQ ID NO:9.
SEQ ID NO:11 comprises a AG006 coding region.
SEQ ID NO:12 comprises an amino acid sequence encoded by coding region of SEQ ID NO:11.

DETAILED DESCRIPTION OF THE INVENTION

Essentiality of the AG001, AG002, AG003, AG004, AG005 and AG006 Genes in *Ashbya gossypii* Demonstrated by Gene Disruption Owing to the provision within the scope of this invention of a novel and powerful gene disruption process, there is no longer a need to know the exact biological function of the protein product encoded by a gene comprising one of the *A. gossypii* DNA sequences provided herein. As shown in the examples below, the identification of novel gene structures, as well as the essentiality of the AG001, AG002, AG003, AG004, AG005 and AG006 genes for norma growth and development, have been demonstrated for the first time in *Ashbya gossypii* using gene disruption techniques. Having established the essentiality of AG001, AG002, AG003, AG004, AG005 and AG006 function in fungi and having identified the nucleic acid sequences encoding these essential activities, the inventors thereby provide an important and sought after tool for new pesticide, particularly fungicide, development.

Recombinant Production of and Uses Thereof

For recombinant production of AG001, AG002, AG003, AG004, AG005 and AG006 in a host organism, a nucleotide sequence encoding AG001, AG002, AG003, AG004, AG005 or AG006 protein is inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements operably linked in proper reading frame, may be inserted into a vector capable of being transformed into the host cell. Suitable expression vectors and methods for recombinant production of proteins are well known for host organisms such as *E. coli,* yeast, and insect cells (see, e.g., Luckow and Summers, Bio/Technol. 6: 47 (1988), and baculovirus expression vectors, e.g., those derived from the genome of Autographica californica nuclear polyhedrosis virus (AcMNPV). A preferred baculovirus/insect system is pAcHLT (Pharmingen, San Diego, Calif.) used to transfect Spodoptera frugiperda Sf9 cells (ATCC) in the presence of linear Autographa californica baculovirus DNA (Pharmigen, San Diego, Calif.). The resulting virus is used to infect HighFive Tricoplusia ni cells (Invitrogen, La Jolla, Calif.). Further preferred expression systems are commercially available such as Baculovirus expression systems: MaxBac 2.0 kit; Invitrogen, Calsbad, Calif.; BACPAK™ Baculovirus Expression System; CLONTECH™, Palo Alto, Calif.; for Yeast expression vectors: pYEUra3; CLONTECH™, Palo Alto, Calif.; EASYSELECT™ Pichia expression kit; Invitrogen, Calsbad, Calif.;ESP Yeast Protein Expression and Purification System; Stratagene, La Jolla, Calif.; *E. coli* expression vectors: pKK233-2; CLONTECH™, Palo Alto, Calif.; pET3 series vectors; Stratagene, La Jolla, Calif.

In a preferred embodiment, the nucleotide sequence encoding a protein having AG001, AG002, AG003, AG004, AG005 Or AG006 activity is derived from an eukaryote, such as a mammal, a fly or a yeast, but is preferably derived from a fungus, particularly a filamentous fungus. In a further preferred embodiment, the nucleotide sequence is identical or substantially similar to the nucleotide sequence set forth in SEQ ID NO: 1, SEQ ID NO: 3, SEQ ID NO: 5, SEQ ID NO: 7, SEQ ID NO: 9 or SEQ ID NO: 11, or encodes a protein having AG001, AG002, AG003, AG004, AG005 or AG006 activity, whose amino acid sequence is identical or substantially similar to the amino acid sequence set forth in SEQ ID NO: 2, SEQ ID NO: 4, SEQ ID NO: 6, SEQ ID NO: 8, SEQ ID NO: 10 or SEQ ID NO: 12 respectively. The nucleotide sequences set forth in SEQ ID NO: 1, SEQ ID NO: 3, SEQ ID NO: 5, SEQ ID NO: 7, SEQ ID NO: 9 OR SEQ ID NO: 11 encode the protein comprising amino acid sequence is set forth in SEQ ID NO: 2, SEQ ID NO: 4, SEQ ID NO: 6, SEQ ID NO: 8, SEQ ID NO: 10 OR SEQ ID NO: 12. In another preferred embodiment, the nucleotide sequence is derived from a prokaryote, preferably a bacteria.

Recombinantly produced AG001, AG002, AG003, AG004, AG005, or AG006 is isolated and purified using a variety of standard techniques. The actual techniques that may be used will vary depending upon the host organism used, whether the protein is designed for secretion, and other such factors familiar to the skilled artisan (see, e.g. chapter 16 of Ausubel, F. et al., "Current Protocols in Molecular Biology", pub. by John Wiley & Sons, Inc. (1994).

Assays for Characterizing the AG001, AG002, AG003, AG004, AG005 and AG006 Proteins Recombinantly produced AG001, AG002, AG003, AG004, AG005 and AG006 proteins are useful for a variety of purposes. For example, they can be used in in vitro assays to screen known pestcidal, particularly fungicidal chemicals whose target has not been identified to determine if they inhibit AG001, AG002, AG003, AG004, AG005 or AG6. Such in vitro assays may also be used as more general screens to identify chemicals that inhibit such enzymatic activities and that are therefore novel pesticide, particularly fungicide, candidates. Alternatively, recombinantly produced AG001, AG002, AG003, AG004, AG005 or AG006 proteins may be used to elucidate the complex structure of these molecules and to further characterize their association with known inhibitors in order to rationally design new inhibitory pesticides, particularly fungicides. Nucleotide sequences substantially similar to SEQ ID NO: 1, SEQ ID NO: 3, SEQ ID NO: 5, SEQ ID NO: 7, SEQ ID NO: 9 OR SEQ ID NO: 11 and proteins substantially similar to SEQ ID NO: 2, SEQ ID NO: 4, SEQ ID NO: 6, SEQ ID NO: 8, SEQ ID NO: 10 OR SEQ ID NO: 12 from any source, including microbial sources, can be used in the assays exemplified herein. Desirably such nucleotide sequences and proteins are derived from fungi. More desirably, they are derived from filamentous fungi, particularly *Ashbya gossypii.* Alternatively, such nucleotide sequences and proteins are derived from non-yeast sources, alternatively from non-*Saccharomyces cervisiae* sources.

A simple assay can be developed to screen for compounds that affect normal functioning of the fungal-encoded activity. Such compounds are promising in vitro leads that can be tested for in vivo pesticidal, particularly fungicidal, activity. A nucleic acid sequence of the invention according to any one of the sequences SEQ ID NO: 1, SEQ ID NO: 3, SEQ ID NO: 5, SEQ ID NO: 7, SEQ ID NO: 9 OR SEQ ID NO: 11 may be operably linked to a strong inducible promoter, such promoters being known in the art. The vector comprising the selected gene of the invention operably linked to the selected inducible promoter may be transformed into bacteria, such as *E. coli.* Transformed *E. coli* harboring and functionally overexpressing expressing a AG001, AG002, AG003, AG004, AG005 or AG006 gene may be grown in a 96-well form automated high-throughput screening where inducible over expression of the selected gene is lethal or suppresses growth of the host. Compounds that are effective in blocking function of the AG001, AG002, AG003, AG004, AG005 or AG006 protein results in bacterial growth. This growth is measured by simple turbidometric means.

In another embodiment, an assay for inhibitors of the AG001, AG002, AG003, AG004, AG005 or AG006 activities uses transgenic fungi or fungal cells capable of overexpressing a nucleotide sequence having AG001, AG002, AG003, AG004, AG005 or AG006 activity respectively operably linked to a strong inducible promoter e.g. , wherein the selected gene product is enzymatically active in the transgenic fungi and/or fungal cells and inducible overexpression of the gene inhibits and/or suppresses growth and/or development of the fungus. The nucleotide sequence is preferably derived from an eukaryote, such as a yeast, but is preferably derived from a fungus and more particularly from a filamentous fungus. In a further preferred embodiment, the nucleic acid sequences set forth in SEQ ID NO: 1, SEQ ID NO: 3, SEQ ID NO: 5, SEQ ID NO: 7, SEQ ID NO: 9 OR SEQ ID NO: 11 SEQ ID NO: 1, SEQ ID NO: 3, SEQ ID NO: 5, SEQ ID NO: 7, SEQ ID NO: 9 OR SEQ ID NO: 11 encode enzymes having AG001, AG002, AG003, AG004, AG005 or AG006 activity respectivelyy, whose amino acid sequence is identical or substantially similar to the amino acid sequence set forth in SEQ ID NO: 2, SEQ ID NO: 4, SEQ ID NO: 6, SEQ ID NO: 8, SEQ ID NO: 10 OR SEQ ID NO: 12. The transgenic fungus or fungal cells are grown in 96-well format microtiter dishes for high-throughput screening. Compounds that are effective in blocking function of the AG001, AG002, AG003, AG004, AG005 or AG006 protein results in fungal growth. This growth is measured by methods known in the art. In a particular embodiment the transgenic fungus is *Ashbya gossypii*.

Similar assays based on expression of the fungal genes of the invention in yeast, using appropiate expression systems as described above may also be used.

In Vitro Inhibitor Assays: Discovery of Small Molecule Ligand that Interacts with Protein of Unknown Function Novel technologies are being examined that can detect interactions between a protein and a ligand without knowing the biological function of the protein. A short description of three methods is presented, including fluorescence correlation spectroscopy, surface-enhanced laser desorption/ionization, and biacore technologies. Many more of these methods are currently being discovered, and some may be amenable to automated, large scale screening in light of this disclosure.

Fluorescence Correlation Spectroscopy (FCS) theory was developed in 1972 but it is only in recent years that the technology to perform FCS became available (Madge et al. (1972) Phys. Rev. Lett., 29: 705–708; Maiti et al. (1997) Proc. Natl. Acad. Sci. USA, 94: 11753–11757). FCS measures the average diffusion rate of a fluorescent molecule within a small sample volume. The sample size can be as low as 103 fluorescent molecules and the sample volume as low as a the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding.

Surface-Enhanced Laser Desorption/Ionization (SELDI) was invented by Hutchens and Yip during the late 1980's (Hutchens and Yip (1993) Rapid Commun. Mass Spectrom. 7: 576–580). When coupled to a time-of-flight mass spectrometer (TOF), SELDI provides a mean to rapidly analyze molecules retained on a chip. It can be applied to ligand-protein interaction analysis by covalently binding the target protein on the chip and analyze by MS the small molecules retained by this protein (Worrall et al. (1998) Anal. Biochem. 70: 750–756). Biacore relies on changes in the refractive index at the surface layer upon binding of a ligand to a protein immobilized on the layer. In this system, a collection of small ligands is injected sequentially in a 2–5 ul cell with the immobilized protein. Binding is detected by surface plasmon resonance (SPR) by recording laser light refracting from the surface. In general, the refractive index change for a given change of mass concentration at the surface layer, is practically the same for all proteins and peptides, allowing a single method to be applicable for any protein (Liedberg et al. (1983) Sensors Actuators 4: 299–304; Malmquist (1993) Nature, 361: 186–187).

IV. In Vivo Inhibitor Assay

In one embodiment, a suspected pesticide, particularly fungicide, for example identified by in vitro screening, is applied to fungi at various concentrations. After application of the suspected fungicide, its effect on the fungus, for example inhibition or suppression of growth and development is recorded.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by Sambrook, et al., Molecular Cloning, eds., Cold Spring Harbor Laboratory Press, Cold Spring Harbor, N.Y. (1989) and by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987), Construction and characterization of a Genomic Library of *A. gossypii* (strain ATCC10895), identification of ORF and promoters is described in U.S. patent application Ser. No: 08/998,416 which is hereby incorporated by reference in its entirety.

Example 1

Identification of Antifungal Drug Targets Represented in the Sequence Listing

Gene disruptions of *Ashbya gossypii* genes are generated by a method using short flanking homology regions to produce gene targeting events. The short flanking homology regions are included within polymerase chain reaction primers of 65 nucleotide overall sequence length. Each of these 65-mers contains approximately 45 nucleotides homology to the target gene locus the target gene locus being identified as described in U.S. patent application Ser. No. 08/998,416 now U.S. Pat. No. 6,239,264 incorporated above by reference, and 20 nucleotides homology (invariant) to a geneticin resistance gene module (also described in U.S. patent application Ser. No. 08/998,416 now U.S. Pat. No. 6,239,264 previously incorporated by reference), with one primer (designated S1) anchored to the 5' end of the geneticin resistance module (using the invariant sequence 5'-GCTAGGGATAACAGGGTAAT-3') (SEQ ID NO:13) and the other primer of the pair (designated S2) anchored to the 3' end of the geneticin resistance module (using the invariant sequence 5'-AGGCATGCAAGCTTAGATCT-3') (SEQ ID NO:14). The PCR product resulting from the amplification of the geneticin resistance module with such an S1/S2 primer pair thus consists of the module flanked by short flanking homology regions of ca. 45 nucleotides specific to the chosen gene disruption site.

Once an S1/S2 primer pair is designed for a particular gene target, approximately 10 ug of the desired geneticin resistance module is obtained by linearizing a vector containing the geneticin resistance gene positioned behind the an appropriate fungal promoter (for example, the *Saccharomyces cerevisiae* TEF1 promoter) and subjecting the linearized template to approximately 35 rounds of a PCR reaction consisting of the following steps: Step 1: Denaturation at 96C. for 30 seconds; Step 2: Primer annealing at 50 C for 30 seconds; Step 3: Elongation reaction at 72 C. for 2.5 minutes. Following the 35th round of this protocol, a final elongation period of 5 minutes at 72 C. is carried out.

Transformation of the PCR product resulting from amplification with the S1/S2 primer pair is done by electroporation as follows: 1) Inoculate 100 ml of AFM media (1% casein peptone, 2% glucose, 1% yeast extract, 0.1% myo-inositol) with an Ashbya spore suspension of approximately $10^7$ spores. 2) Incubate at 30 C. for a maximum of 18 hors at a shaker speed of 200 rpm. 3) Collect the resultant fungal mycelia by filtration and wash once with sterile water. 4) Resuspend 1 gram of mycelia (wet weight) in 40 ml of 50 mM potassium phosphate buffer, pH 7.5 containing 25 mM DTT and incubate at 30 C. for 30 minutes with gentle shaking. 5) Collect the mycelia by filtration and wash once with 50 ml of cold STM buffer (275 mM sucrose, 10 mM Tris-HCl, pH 7.5, 2 mM $MgCl_2$). 6) Resuspend the mycelia to a dense mixture in STM buffer. 7) Mix approximately 150 ul of the mycelial mixture with 10 ug of PCR product (in a maximum volume of 50 ul) in an Eppendorf tube and transfer the mixture to an electroporation cuvette with a 4 mM gap distance. 8) Apply an electric field pulse of 1.5 kV, 100 ohms, 25 uF which will result in a pulse length of approximately 2.3 milliseconds. Add 1 ml of AFM media to the cuvette and spread equal amounts onto 3 pre-dried AFM agar plates. 9) Incubate plates for a minimum of 4 hours at 30 C. 10) Overlay the plates with 8 ml of a 0.5% agarose toplayer containing Geneticin/G418 at a final concentration of 200 ug/ml. 11) Incubate at 30 C. for approximately 3 days to allow sufficient growth of geneticin resistant transformants.

Verification of the desired transformation event resulting in homologous integration of the geneticin resistance module in the target of interest is achieved by PCR using verification primers designated G1 (positioned upstream of the S1 region) and G4 (positioned downstream of the S2 region) and template DNA purified from putative Ashbya transformants. Additional verification primers designated G2 (5'-GTTTAGTCTGACCATCTCATCTG-3') (SEQ ID NO:15) and G3 (5'-TCGCAGACCGATACCAGGATC-3') (SEQ ID NO:16) are derived from the open reading frame of the selectable geneticin resistance gene such that the detection of a G1/G2 PCR product and or a G3/G4 PCR product of a predictable size serves to verify the desired gene disruption event. Also, verification of the desired gene disruption can be determined by standard DNA hybridization experiments.

Determination of whether a gene is essential to growth of Ashbya can be achieved by the following analysis. The transformation of DNA fragments described above utilizes multinucleate Ashbya mycelia as recipients. Therefore a primary transformant able to grow on geneticin containing media originates as a mycelium containing cells at least one of which has at least one transformed nucleus, but usually containing non-transformed nuclei as well. Thus, if an essential gene is disrupted in the transformed nucleus, the essential gene product can, in many instances, still be supplied by the non-transformed nuclei within the same cell. Such primary transformants usually exhibit normal growth and sporulation, and spores are collected from primary transformants allowed to grow at 30 C. for at least 5 days. Since spores are uninucleate, however, transformants which have an essential gene disrupted in nuclei containing the geneticin resistance cartridge will fail to yield spores which grow normally, if at all, on geneticin-containing media.

S1 and S2 primer pairs usable to generate disruptions of the indicated genes are as follows:

AG001: S1:
  5'-AGGACCACTAGCTCGTTGCGCTGCAATATAATA ATAAGAACGAGA GCTAGGGATAACAGGGTAAT-3' (SEQ ID NO:17)
  S2:
  5'-AAGTATTCAATCAACTATGTGAGTAGTTTCTT GTAGGCAGTCTCC AGGCATGCAAGCTTAGATCT-3'(SEQ ID NO:18)
AG002: S1:
  5'-CTGGCATCAGAGGAAGCTCCCACCACCAAGCT CTACAAACACAAG GCTAGGGATAACAGGGTAAT-3'(SEQ ID NO:19)
  S2:
  5'-ATTATATTAGTATAGTCTAAAGTTGCAGGCAG TGGGTATTAAAGT AGGCATGCAAGCTTAGATCT-3'(SEQ ID NO:20)
AG003: S1:
  5'-ACTTGCGTACTCTTTCGCGTGCTCGTCAGCCAC CGAACAACGCAG GCTAGGGATAACAGGGTAAT-3' (SEQ ID NO:21)
  S2:
  5'-TTAAAGAATGATAAAGAACCAAAAACACCA CGAGCTTGCATAACA AGGCATGCAAGCTTAGATCT-3'(SEQ ID NO:22)
AG004: S1:
  5'-GTGCGTGTCAGCGAGCATCTAATCAAGCTGCA AGGCGCCGGAAAT GCTAGGGATAACAGGGTAAT-3'(SEQ ID NO:23)
  S2:
  5'-TTATCACATATTTCTAAGTTAATAGATATTTTT ACTTAGTATGAA AGGCATGCAAGCTTAGATCT-3'(SEQ ID NO:24)
AG006: S1:
  5'-GAGAGAGACGCTACGGTACTACGAATTTCTCT GTAGAGTTGGAGA GCTAGGGATAACAGGGTAAT-3'(SEQ ID NO:25)
  S2: 5'-TACTATTGAGAATGTTCGCGACTGCATGTAA AGTCTCAAAAACTT AGGCATGCAAGCTTAGATCT-3'(SEQ ID NO:26)
AG005: S1:
  5'-AAATATAATAAAAATTGACAACTGGCTAGAAGT GATACCGCAGTT GCTAGGGATAACAGGGTAAT-3' (SEQ ID NO:27)
  S2:
  5'-CCTCTTATAGTTCATGACCCATTCATATGCGT CATTCAGGTCTCT AGGCATGCAAGCTTAGATCT-3'(SEQ ID NO:28)

The above disclosed embodiments are illustrative. This disclosure of the invention will place one skilled in the art in possession of many variations of the invention. All such obvious and foreseeable variations are intended to be encompassed by the appended claims.

What is claimed is:

1. An isolated nucleotide sequence consisting essentially of SEQ ID NO: 1.

2. The isolated nucleotide sequence of claim 1, wherein the nucleotide sequence is SEQ ID NO: 1.

3. The isolated nucleotide sequence of claim 1, wherein the nucleotide sequence is a fungal nucleotide sequence.

4. The isolated nucleotide sequence of claim 3, wherein the fungus is *Ashbya gossypii*.

5. The isolated nucleotide sequence of claim 1, wherein the nucleotide sequence encodes an amino acid sequence consisting essentially of SEQ ID NO: 2.

6. An isolated nucleotide sequence encoding an amino acid sequence according to SEQ ID NO: 2.

* * * * *

SEQUENCE LISTING

<160> NUMBER OF SEQ ID NOS: 28

<210> SEQ ID NO 1
<211> LENGTH: 624
<212> TYPE: DNA
<213> ORGANISM: Ashbya gossypii
<220> FEATURE:
<221> NAME/KEY: CDS
<222> LOCATION: (1)..(624)

<400> SEQUENCE: 1

-continued

```
atg tct cag caa atg cat aac ccc agt atc agg aga aaa ttg gtg atc     48
Met Ser Gln Gln Met His Asn Pro Ser Ile Arg Arg Lys Leu Val Ile
1               5                   10                  15 gtc gga gat ggt gca tgc ggg aaa aca tgt ctt ttg att gtg ttt gcc     96
Val Gly Asp Gly Ala Cys Gly Lys Thr Cys Leu Leu Ile Val Phe Ala
            20                  25                  30 aag gga aag ttc cca cag gtg tat gtt cct acg gtt ttc gac aac tac    144
Lys Gly Lys Phe Pro Gln Val Tyr Val Pro Thr Val Phe Asp Asn Tyr
        35                  40                  45 gtt gca gat gtg gag gta gac ggc aga cgg gtg gag ctt gcg ctt tgg    192
Val Ala Asp Val Glu Val Asp Gly Arg Arg Val Glu Leu Ala Leu Trp
50                  55                  60 gat acg gct ggg cag gag gat tac gac agg cta cgg ccg tta tcg tac    240
Asp Thr Ala Gly Gln Glu Asp Tyr Asp Arg Leu Arg Pro Leu Ser Tyr
65                  70                  75                  80 cca gac tcc aat gtt gtg ttg atc tgc tac tcg att gac cta cca gac    288
Pro Asp Ser Asn Val Val Leu Ile Cys Tyr Ser Ile Asp Leu Pro Asp
            85                  90                  95 tcg ttg gag aac gtg atg gag aag tgg atc agc gag gtg cta tac ttc    336
Ser Leu Glu Asn Val Met Glu Lys Trp Ile Ser Glu Val Leu Tyr Phe
        100                 105                 110 tgc cag ggt gtt ccg atc atc ttg gtg ggg tgc aag gct gac ttg cgg    384
Cys Gln Gly Val Pro Ile Ile Leu Val Gly Cys Lys Ala Asp Leu Arg
    115                 120                 125 aac gat ccg caa gtg atc gag cag ttg aga cag cag gga cag cag cct    432
Asn Asp Pro Gln Val Ile Glu Gln Leu Arg Gln Gln Gly Gln Gln Pro
130                 135                 140 gtc tcg cag gct cag gcg cag gag gta gcg gac cag atc ggc gcg gta    480
Val Ser Gln Ala Gln Ala Gln Glu Val Ala Asp Gln Ile Gly Ala Val
145                 150                 155                 160 gag tac att gag tgc tct gca aag acc ggc ttt ggt gtg cgc gag gtg    528
Glu Tyr Ile Glu Cys Ser Ala Lys Thr Gly Phe Gly Val Arg Glu Val
                165                 170                 175 ttt gag gcg gcc acg cgt gct tcc ttg atg ggg aaa caa ggc aag tct    576
Phe Glu Ala Ala Thr Arg Ala Ser Leu Met Gly Lys Gln Gly Lys Ser
            180                 185                 190 aag gcg aag tct gac aag aag aag aag aaa aag tgt gtg gtc ttg tag    624
Lys Ala Lys Ser Asp Lys Lys Lys Lys Lys Cys Val Val Leu
        195                 200                 205
```

<210> SEQ ID NO 2
<211> LENGTH: 207
<212> TYPE: PRT
<213> ORGANISM: Ashbya gossypii

<400> SEQUENCE: 2

```
Met Ser Gln Gln Met His Asn Pro Ser Ile Arg Arg Lys Leu Val Ile
1               5                   10                  15

Val Gly Asp Gly Ala Cys Gly Lys Thr Cys Leu Leu Ile Val Phe Ala
            20                  25                  30

Lys Gly Lys Phe Pro Gln Val Tyr Val Pro Thr Val Phe Asp Asn Tyr
        35                  40                  45

Val Ala Asp Val Glu Val Asp Gly Arg Arg Val Glu Leu Ala Leu Trp
    50                  55                  60

Asp Thr Ala Gly Gln Glu Asp Tyr Asp Arg Leu Arg Pro Leu Ser Tyr
65                  70                  75                  80

Pro Asp Ser Asn Val Val Leu Ile Cys Tyr Ser Ile Asp Leu Pro Asp
                85                  90                  95
```

```
Ser Leu Glu Asn Val Met Glu Lys Trp Ile Ser Glu Val Leu Tyr Phe
            100                 105                 110

Cys Gln Gly Val Pro Ile Ile Leu Val Gly Cys Lys Ala Asp Leu Arg
            115                 120                 125

Asn Asp Pro Gln Val Ile Glu Gln Leu Arg Gln Gln Gly Gln Gln Pro
            130                 135                 140

Val Ser Gln Ala Gln Ala Gln Val Ala Asp Gln Ile Gly Ala Val
145                 150                 155                 160

Glu Tyr Ile Glu Cys Ser Ala Lys Thr Gly Phe Gly Val Arg Glu Val
                    165                 170                 175

Phe Glu Ala Ala Thr Arg Ala Ser Leu Met Gly Lys Gln Gly Lys Ser
            180                 185                 190

Lys Ala Lys Ser Asp Lys Lys Lys Lys Lys Cys Val Val Leu
            195                 200                 205

<210> SEQ ID NO 3
<211> LENGTH: 675
<212> TYPE: DNA
<213> ORGANISM: Ashbya gossypii
<220> FEATURE:
<221> NAME/KEY: CDS
<222> LOCATION: (1)..(675)

<400> SEQUENCE: 3 atg cct ctg tgt ggg tcg agc tcg tcg tcg aag cat cct atc gag cgc     48
Met Pro Leu Cys Gly Ser Ser Ser Ser Lys His Pro Ile Glu Arg
  1               5                  10                  15 aag atc gtc atc ctc gga gac ggt gct tgc ggg aag acg tcg ctg ttg     96
Lys Ile Val Ile Leu Gly Asp Gly Ala Cys Gly Lys Thr Ser Leu Leu
                 20                  25                  30 aac gtg ttc acg cga ggg tac ttt ccg aag gtg tac gag ccc acg gta    144
Asn Val Phe Thr Arg Gly Tyr Phe Pro Lys Val Tyr Glu Pro Thr Val
             35                  40                  45 ttc gaa aac tac atc cat gac atc ttc gtg gac aac cag cac atc acg    192
Phe Glu Asn Tyr Ile His Asp Ile Phe Val Asp Asn Gln His Ile Thr
 50                  55                  60 ctg agc ctg tgg gac act gct ggg cag gag gag ttt gac cgg ttg cga    240
Leu Ser Leu Trp Asp Thr Ala Gly Gln Glu Glu Phe Asp Arg Leu Arg
 65                  70                  75                  80 tcg ctg tcg tac tcg gac aca cac acg att atg ctg tgt ttc tcg gtg    288
Ser Leu Ser Tyr Ser Asp Thr His Thr Ile Met Leu Cys Phe Ser Val
                 85                  90                  95 gac tcg cgg gac tcg ctg gag aac gtc aag aac aag tgg gtg agc gaa    336
Asp Ser Arg Asp Ser Leu Glu Asn Val Lys Asn Lys Trp Val Ser Glu
            100                 105                 110 att gcg gac cac tgc gag ggc gtg aag ctg gtg cta gtg gcg ctg aag    384
Ile Ala Asp His Cys Glu Gly Val Lys Leu Val Leu Val Ala Leu Lys
            115                 120                 125 tgc gac ttg cgc agc agc gac gag tac ggc aac gag agc gcc atc acg    432
Cys Asp Leu Arg Ser Ser Asp Glu Tyr Gly Asn Glu Ser Ala Ile Thr
130                 135                 140 ccg ggg tcc atc cag aac cag aag tac aac ggc ggc ggc aac ggg        480
Pro Gly Ser Ile Gln Asn Gln Lys Tyr Asn Gly Gly Gly Asn Gly
145                 150                 155                 160 ctg atc ccc tac gac gag ggg ctg gcg atg gcc aag cag att ggg gcg    528
Leu Ile Pro Tyr Asp Glu Gly Leu Ala Met Ala Lys Gln Ile Gly Ala
                165                 170                 175 ctg cgc tat ctg gag tgc agc gcc aag atg aac cgt ggc gtg aac gag    576
Leu Arg Tyr Leu Glu Cys Ser Ala Lys Met Asn Arg Gly Val Asn Glu
            180                 185                 190
```

-continued

```
gcg ttc acc gag gct gcg cgc tgc gcg ctg act gcg aca ccg aag ggg      624
Ala Phe Thr Glu Ala Ala Arg Cys Ala Leu Thr Ala Thr Pro Lys Gly
        195                 200                 205 gcc cgg gac tct gcg ccc gag gcc gaa agc agc agt tgt act atc atg      672
Ala Arg Asp Ser Ala Pro Glu Ala Glu Ser Ser Ser Cys Thr Ile Met
210                 215                 220 tga                                                                   675
```

<210> SEQ ID NO 4
<211> LENGTH: 224
<212> TYPE: PRT
<213> ORGANISM: Ashbya gossypii

<400> SEQUENCE: 4

```
Met Pro Leu Cys Gly Ser Ser Ser Ser Lys His Pro Ile Glu Arg
 1               5                  10                  15

Lys Ile Val Ile Leu Gly Asp Gly Ala Cys Gly Lys Thr Ser Leu Leu
             20                  25                  30

Asn Val Phe Thr Arg Gly Tyr Phe Pro Lys Val Tyr Glu Pro Thr Val
         35                  40                  45

Phe Glu Asn Tyr Ile His Asp Ile Phe Val Asp Asn Gln His Ile Thr
     50                  55                  60

Leu Ser Leu Trp Asp Thr Ala Gly Gln Glu Glu Phe Asp Arg Leu Arg
 65                  70                  75                  80

Ser Leu Ser Tyr Ser Asp Thr His Thr Ile Met Leu Cys Phe Ser Val
                 85                  90                  95

Asp Ser Arg Asp Ser Leu Glu Asn Val Lys Asn Lys Trp Val Ser Glu
            100                 105                 110

Ile Ala Asp His Cys Glu Gly Val Lys Leu Val Leu Val Ala Leu Lys
        115                 120                 125

Cys Asp Leu Arg Ser Ser Asp Glu Tyr Gly Asn Glu Ser Ala Ile Thr
    130                 135                 140

Pro Gly Ser Ile Gln Asn Gln Lys Tyr Asn Gly Gly Gly Asn Gly
145                 150                 155                 160

Leu Ile Pro Tyr Asp Glu Gly Leu Ala Met Ala Lys Gln Ile Gly Ala
                165                 170                 175

Leu Arg Tyr Leu Glu Cys Ser Ala Lys Met Asn Arg Gly Val Asn Glu
            180                 185                 190

Ala Phe Thr Glu Ala Ala Arg Cys Ala Leu Thr Ala Thr Pro Lys Gly
        195                 200                 205

Ala Arg Asp Ser Ala Pro Glu Ala Glu Ser Ser Ser Cys Thr Ile Met
    210                 215                 220
```

<210> SEQ ID NO 5
<211> LENGTH: 6216
<212> TYPE: DNA
<213> ORGANISM: Ashbya gossypii
<220> FEATURE:
<221> NAME/KEY: CDS
<222> LOCATION: (1)..(6216)

<400> SEQUENCE: 5

```
atg ccc cta aag tgg gct gcg aga aac aag aag cca cca tct gcg ccg      48
Met Pro Leu Lys Trp Ala Ala Arg Asn Lys Lys Pro Pro Ser Ala Pro
 1               5                  10                  15 cag tcg tgc gca agc aag ccg tcc agt gcg tcg cag tca tcc tgc gtt      96
Gln Ser Cys Ala Ser Lys Pro Ser Ser Ala Ser Gln Ser Ser Cys Val
             20                  25                  30
```

```
gac gag cgc atc agc gcg acg ccg cgg agc tcg atc tcg tcg aat tca    144
Asp Glu Arg Ile Ser Ala Thr Pro Arg Ser Ser Ile Ser Ser Asn Ser
             35                  40                  45 agc cct aat tcc aaa aat aat atg tcg cgt cat tcg cac tcc aat gga    192
Ser Pro Asn Ser Lys Asn Asn Met Ser Arg His Ser His Ser Asn Gly
         50                  55                  60 tct gtt tac tca gat gaa aca aca ttg aag aca gcc caa acc cac tac    240
Ser Val Tyr Ser Asp Glu Thr Thr Leu Lys Thr Ala Gln Thr His Tyr
 65              70                  75                  80 aca caa caa ggc caa cag gca aag ccg caa cag cac acg cag cag cag    288
Thr Gln Gln Gly Gln Gln Ala Lys Pro Gln Gln His Thr Gln Gln Gln
                 85                  90                  95 cag cag cag cca cag acg ccg atg cag tta cag gtg ccg acg ggg caa    336
Gln Gln Gln Pro Gln Thr Pro Met Gln Leu Gln Val Pro Thr Gly Gln
                100                 105                 110 gcg cac aag cgg acg ctg aca tgt gag gac atg aag gcg ggt gcg cgc    384
Ala His Lys Arg Thr Leu Thr Cys Glu Asp Met Lys Ala Gly Ala Arg
            115                 120                 125 tgc gag gag cag gtg tcg ccc tgc tcg cag ccg gcg ggc tcg ccg gtg    432
Cys Glu Glu Gln Val Ser Pro Cys Ser Gln Pro Ala Gly Ser Pro Val
130                 135                 140 cga cgt gga ggc ggg ctg aac ggg gag acg tac gac ggg act gtg ttt    480
Arg Arg Gly Gly Gly Leu Asn Gly Glu Thr Tyr Asp Gly Thr Val Phe
145                 150                 155                 160 cgg ctc ggg tgg gtg aac aag gcg cag ggc gca gcg ccg gcg cgc gag    528
Arg Leu Gly Trp Val Asn Lys Ala Gln Gly Ala Ala Pro Ala Arg Glu
                165                 170                 175 ggg cga tac agc cac cag cca aca gcg tca ctg tct tcg atc gga tcg    576
Gly Arg Tyr Ser His Gln Pro Thr Ala Ser Leu Ser Ser Ile Gly Ser
            180                 185                 190 gag cgg ccg cac ttc acg gga ggg ggg acg agc ggg tac cag tat gtc    624
Glu Arg Pro His Phe Thr Gly Gly Gly Thr Ser Gly Tyr Gln Tyr Val
        195                 200                 205 gcg act gcg tac cgg ttg cac cgt gcg cag ctc aag ggc tgc atc ctg    672
Ala Thr Ala Tyr Arg Leu His Arg Ala Gln Leu Lys Gly Cys Ile Leu
    210                 215                 220 aat ctg tac aag tcg ggc ctg acg aat gtg aag tac ttc gac ccg gcg    720
Asn Leu Tyr Lys Ser Gly Leu Thr Asn Val Lys Tyr Phe Asp Pro Ala
225                 230                 235                 240 ctg gag ccg agc gct gcg gcg ctg cag atg cac cag gag cga cag gag    768
Leu Glu Pro Ser Ala Ala Ala Leu Gln Met His Gln Glu Arg Gln Glu
                245                 250                 255 atg ccc ctc ctg cag ccg ccc ctc ccc tcc gag gct gtg ccg gcg cct    816
Met Pro Leu Leu Gln Pro Pro Leu Pro Ser Glu Ala Val Pro Ala Pro
            260                 265                 270 tcg atc ctg gag gcg tcc atg gag agc ggc gag ctg cgg ctg gag tac    864
Ser Ile Leu Glu Ala Ser Met Glu Ser Gly Glu Leu Arg Leu Glu Tyr
        275                 280                 285 ctg agc gag gcg tac cct cat ccg gac cta cag ctg gac aag aag gac    912
Leu Ser Glu Ala Tyr Pro His Pro Asp Leu Gln Leu Asp Lys Lys Asp
    290                 295                 300 ggc aag atc ctt tcg ggg tcg ctg gag tcg ctg tgc cac gcc gtg ctg    960
Gly Lys Ile Leu Ser Gly Ser Leu Glu Ser Leu Cys His Ala Val Leu
305                 310                 315                 320 ttc atg ccc acg act gac gcg aaa cgg gtc aca gac atc ttg ttg ctc   1008
Phe Met Pro Thr Thr Asp Ala Lys Arg Val Thr Asp Ile Leu Leu Leu
                325                 330                 335 ctg ccg ctc ctg gac gac ttc acg cgt gtc ctc aac tac ttc aac ctg   1056
Leu Pro Leu Leu Asp Asp Phe Thr Arg Val Leu Asn Tyr Phe Asn Leu
```

-continued

|  | 340 |  |  |  | 345 |  |  |  | 350 |  |  |  |  |  |  |
|---|---|---|---|---|---|---|---|---|---|---|---|---|---|---|---|
| ttc | ggg | aag | gta | ttt | tcg | aag | cac | cac | ccg | gcg | ggc | gcg | gga | gcc | 1104 |
| Phe | Gly | Lys | Val | Phe | Ser | Lys | His | His | Pro | Ala | Gly | Ala | Gly | Ala |  |
|  |  | 355 |  |  |  |  | 360 |  |  |  |  | 365 |  |  |  |

| gat | gac | cta | aat | cag | aac | tac | aac | atc | agc | aac | gag | aca | gac | cgc | caa | 1152 |
|---|---|---|---|---|---|---|---|---|---|---|---|---|---|---|---|---|
| Asp | Asp | Leu | Asn | Gln | Asn | Tyr | Asn | Ile | Ser | Asn | Glu | Thr | Asp | Arg | Gln |  |
|  | 370 |  |  |  |  | 375 |  |  |  |  | 380 |  |  |  |  |  |

| ttg | acg | ctg | cgg | cta | gcc | aca | gtg | gtc | cag | aca | gtg | ctg | gac | atg | ttc | 1200 |
|---|---|---|---|---|---|---|---|---|---|---|---|---|---|---|---|---|
| Leu | Thr | Leu | Arg | Leu | Ala | Thr | Val | Val | Gln | Thr | Val | Leu | Asp | Met | Phe |  |
| 385 |  |  |  |  | 390 |  |  |  |  | 395 |  |  |  |  | 400 |  |

| ccg | ggc | ttt | ctg | ctg | gac | gac | aag | att | ttc | cag | tcc | ctg | gta | ata | cta | 1248 |
|---|---|---|---|---|---|---|---|---|---|---|---|---|---|---|---|---|
| Pro | Gly | Phe | Leu | Leu | Asp | Asp | Lys | Ile | Phe | Gln | Ser | Leu | Val | Ile | Leu |  |
|  |  |  |  | 405 |  |  |  |  | 410 |  |  |  |  | 415 |  |  |

| ctc | gat | acg | att | tcc | ttc | cac | gat | gaa | gac | acg | tcg | cag | gag | ctg | aag | 1296 |
|---|---|---|---|---|---|---|---|---|---|---|---|---|---|---|---|---|
| Leu | Asp | Thr | Ile | Ser | Phe | His | Asp | Glu | Asp | Thr | Ser | Gln | Glu | Leu | Lys |  |
|  |  |  |  | 420 |  |  |  |  | 425 |  |  |  |  | 430 |  |  |

| gtg | gcg | ata | gcg | gag | aaa | cag | acg | gta | ctg | gtc | aag | ctg | acc | ggc | ttt | 1344 |
|---|---|---|---|---|---|---|---|---|---|---|---|---|---|---|---|---|
| Val | Ala | Ile | Ala | Glu | Lys | Gln | Thr | Val | Leu | Val | Lys | Leu | Thr | Gly | Phe |  |
|  |  |  | 435 |  |  |  |  | 440 |  |  |  |  | 445 |  |  |  |

| gca | aat | gaa | ccc | atc | cag | tcc | gcg | aaa | ctc | gat | gtt | tta | ata | aag | gtg | 1392 |
|---|---|---|---|---|---|---|---|---|---|---|---|---|---|---|---|---|
| Ala | Asn | Glu | Pro | Ile | Gln | Ser | Ala | Lys | Leu | Asp | Val | Leu | Ile | Lys | Val |  |
|  |  | 450 |  |  |  |  | 455 |  |  |  |  | 460 |  |  |  |  |

| cag | agc | ttc | ctg | aaa | ctt | gat | acc | gag | aag | gtt | gcc | aac | cag | att | cac | 1440 |
|---|---|---|---|---|---|---|---|---|---|---|---|---|---|---|---|---|
| Gln | Ser | Phe | Leu | Lys | Leu | Asp | Thr | Glu | Lys | Val | Ala | Asn | Gln | Ile | His |  |
| 465 |  |  |  |  | 470 |  |  |  |  | 475 |  |  |  |  | 480 |  |

| aag | atc | aat | cta | acc | ttt | aat | agg | gta | tgg | agc | cca | caa | gcc | gat | tat | 1488 |
|---|---|---|---|---|---|---|---|---|---|---|---|---|---|---|---|---|
| Lys | Ile | Asn | Leu | Thr | Phe | Asn | Arg | Val | Trp | Ser | Pro | Gln | Ala | Asp | Tyr |  |
|  |  |  |  | 485 |  |  |  |  | 490 |  |  |  |  | 495 |  |  |

| tcc | cta | ctt | tac | gac | tct | caa | tat | aca | caa | aag | cac | gtg | gaa | cta | aac | 1536 |
|---|---|---|---|---|---|---|---|---|---|---|---|---|---|---|---|---|
| Ser | Leu | Leu | Tyr | Asp | Ser | Gln | Tyr | Thr | Gln | Lys | His | Val | Glu | Leu | Asn |  |
|  |  |  | 500 |  |  |  |  | 505 |  |  |  |  | 510 |  |  |  |

| cca | ttg | gta | ttt | ttc | aac | gat | aaa | aat | gta | cag | tat | ttg | agt | cgc | tta | 1584 |
|---|---|---|---|---|---|---|---|---|---|---|---|---|---|---|---|---|
| Pro | Leu | Val | Phe | Phe | Asn | Asp | Lys | Asn | Val | Gln | Tyr | Leu | Ser | Arg | Leu |  |
|  |  | 515 |  |  |  |  | 520 |  |  |  |  | 525 |  |  |  |  |

| atg | gtg | tct | cat | atc | ttc | tgc | gaa | gag | acg | gga | ttt | acg | ccg | aag | aaa | 1632 |
|---|---|---|---|---|---|---|---|---|---|---|---|---|---|---|---|---|
| Met | Val | Ser | His | Ile | Phe | Cys | Glu | Glu | Thr | Gly | Phe | Thr | Pro | Lys | Lys |  |
|  | 530 |  |  |  |  | 535 |  |  |  |  | 540 |  |  |  |  |  |

| cga | gcg | gag | gtt | ttg | aca | aaa | tgg | gtc | caa | ttg | gga | tgc | aag | ttt | gag | 1680 |
|---|---|---|---|---|---|---|---|---|---|---|---|---|---|---|---|---|
| Arg | Ala | Glu | Val | Leu | Thr | Lys | Trp | Val | Gln | Leu | Gly | Cys | Lys | Phe | Glu |  |
| 545 |  |  |  |  | 550 |  |  |  |  | 555 |  |  |  |  | 560 |  |

| cga | ctt | ggg | gac | atg | gtc | tca | tgg | ctt | gca | att | gcg | aca | gta | ata | tgc | 1728 |
|---|---|---|---|---|---|---|---|---|---|---|---|---|---|---|---|---|
| Arg | Leu | Gly | Asp | Met | Val | Ser | Trp | Leu | Ala | Ile | Ala | Thr | Val | Ile | Cys |  |
|  |  |  |  | 565 |  |  |  |  | 570 |  |  |  |  | 575 |  |  |

| tcc | atc | ccc | gtt | tta | cgc | ttg | aca | agg | acg | tgg | caa | tat | gtg | cct | gac | 1776 |
|---|---|---|---|---|---|---|---|---|---|---|---|---|---|---|---|---|
| Ser | Ile | Pro | Val | Leu | Arg | Leu | Thr | Arg | Thr | Trp | Gln | Tyr | Val | Pro | Asp |  |
|  |  |  | 580 |  |  |  |  | 585 |  |  |  |  | 590 |  |  |  |

| tct | tac | ttg | aag | ata | att | ttt | aag | gat | tgg | gta | ccc | acg | att | gtc | cag | 1824 |
|---|---|---|---|---|---|---|---|---|---|---|---|---|---|---|---|---|
| Ser | Tyr | Leu | Lys | Ile | Ile | Phe | Lys | Asp | Trp | Val | Pro | Thr | Ile | Val | Gln |  |
|  |  |  | 595 |  |  |  |  | 600 |  |  |  |  | 605 |  |  |  |

| ttg | gat | cgc | agg | caa | atg | tcc | tcc | aag | tcg | atg | aac | agt | gtt | ttc | ata | 1872 |
|---|---|---|---|---|---|---|---|---|---|---|---|---|---|---|---|---|
| Leu | Asp | Arg | Arg | Gln | Met | Ser | Ser | Lys | Ser | Met | Asn | Ser | Val | Phe | Ile |  |
|  | 610 |  |  |  |  | 615 |  |  |  |  | 620 |  |  |  |  |  |

| cta | gcc | cca | cct | aat | tta | aac | gat | gcc | ttt | gtg | agg | gac | aat | gtg | atc | 1920 |
|---|---|---|---|---|---|---|---|---|---|---|---|---|---|---|---|---|
| Leu | Ala | Pro | Pro | Asn | Leu | Asn | Asp | Ala | Phe | Val | Arg | Asp | Asn | Val | Ile |  |
| 625 |  |  |  |  | 630 |  |  |  |  | 635 |  |  |  |  | 640 |  |

| cct | tac | ttt | ggc | gac | tta | gtc | att | cac | tcc | gat | gat | cta | ccc | aga | gac | 1968 |
|---|---|---|---|---|---|---|---|---|---|---|---|---|---|---|---|---|
| Pro | Tyr | Phe | Gly | Asp | Leu | Val | Ile | His | Ser | Asp | Asp | Leu | Pro | Arg | Asp |  |
|  |  |  |  | 645 |  |  |  |  | 650 |  |  |  |  | 655 |  |  |

| agc | aag | tat | aag | tac | ttg | gag | aaa | aag | ata | cgc | cgc | aca | aaa | aat | gcc | 2016 |
|---|---|---|---|---|---|---|---|---|---|---|---|---|---|---|---|---|

```
Ser Lys Tyr Lys Tyr Leu Glu Lys Lys Ile Arg Arg Thr Lys Asn Ala
        660                 665                 670 ttt tac aag tgg cag cag aga cta gac cag gca ttt gcg cag gat aga    2064
Phe Tyr Lys Trp Gln Gln Arg Leu Asp Gln Ala Phe Ala Gln Asp Arg
            675                 680                 685 gat tct gcc agt tcc ttt acg gac tcc ttg cat ctt gac gag gag gaa    2112
Asp Ser Ala Ser Ser Phe Thr Asp Ser Leu His Leu Asp Glu Glu Glu
        690                 695                 700 cat gat gtg gca gat ttc tat cag tat tgg agg ttt cac atg aat ttg    2160
His Asp Val Ala Asp Phe Tyr Gln Tyr Trp Arg Phe His Met Asn Leu
705                 710                 715                 720 cca cca atg aat att gaa aca att atg gaa atg agt tta aaa atg gaa    2208
Pro Pro Met Asn Ile Glu Thr Ile Met Glu Met Ser Leu Lys Met Glu
                725                 730                 735 ccc cct tct att aat caa cag act tat tcg aag aca tac tca acg aga    2256
Pro Pro Ser Ile Asn Gln Gln Thr Tyr Ser Lys Thr Tyr Ser Thr Arg
            740                 745                 750 agt gcg ctc atc agt ggg gct tat ttg ccg acc ttg ttt aca aca ttg    2304
Ser Ala Leu Ile Ser Gly Ala Tyr Leu Pro Thr Leu Phe Thr Thr Leu
        755                 760                 765 tta cca tca tat tcc ctg ttt cca cag gaa cta ctg att gca gct gca    2352
Leu Pro Ser Tyr Ser Leu Phe Pro Gln Glu Leu Leu Ile Ala Ala Ala
770                 775                 780 agc acg cca tcc acg aaa aat aat aac tca tct caa gcc tct aac cgg    2400
Ser Thr Pro Ser Thr Lys Asn Asn Asn Ser Ser Gln Ala Ser Asn Arg
785                 790                 795                 800 atc agc caa cta tct gtg aat tcg aca cct cac tca aat gcc agt tcg    2448
Ile Ser Gln Leu Ser Val Asn Ser Thr Pro His Ser Asn Ala Ser Ser
                805                 810                 815 agt tcc gca gcg agc gct gtt acc gga att gat aat atc gat gtg cca    2496
Ser Ser Ala Ala Ser Ala Val Thr Gly Ile Asp Asn Ile Asp Val Pro
            820                 825                 830 att aca aag gag ata tca tcc aag tta tca aac aaa cag gtt tta ctg    2544
Ile Thr Lys Glu Ile Ser Ser Lys Leu Ser Asn Lys Gln Val Leu Leu
        835                 840                 845 aag ttc att agg gat atg ttc aac gta gat att aac gtt ttc cac ata    2592
Lys Phe Ile Arg Asp Met Phe Asn Val Asp Ile Asn Val Phe His Ile
850                 855                 860 tct gat gat gtt att ttc aag tcc att cgt gat tac gaa gct aaa tcg    2640
Ser Asp Asp Val Ile Phe Lys Ser Ile Arg Asp Tyr Glu Ala Lys Ser
865                 870                 875                 880 agg cct act agt gtc gtt att gaa agt ccc aag cgg ttg tcg ctt ctt    2688
Arg Pro Thr Ser Val Val Ile Glu Ser Pro Lys Arg Leu Ser Leu Leu
                885                 890                 895 tct tcg gtc tct cct gat gta tct gct gtc agc agt gca ttg gaa aat    2736
Ser Ser Val Ser Pro Asp Val Ser Ala Val Ser Ser Ala Leu Glu Asn
            900                 905                 910 ttg gat ctg ttc aaa aat ttt aac tcc agt tct gat gat atc gcc gaa    2784
Leu Asp Leu Phe Lys Asn Phe Asn Ser Ser Ser Asp Asp Ile Ala Glu
        915                 920                 925 ttt acc gta cag gtg gtg ttg aaa tgt gca agc ttg gaa aag att ttt    2832
Phe Thr Val Gln Val Val Leu Lys Cys Ala Ser Leu Glu Lys Ile Phe
    930                 935                 940 gat atc ttg gtc tta aca agc cgg gtg ttc tcc aac ctc gta aca act    2880
Asp Ile Leu Val Leu Thr Ser Arg Val Phe Ser Asn Leu Val Thr Thr
945                 950                 955                 960 aca gat ttg gtt tcc tat ttt aat agt gaa aag gca agg cgg gaa aag    2928
Thr Asp Leu Val Ser Tyr Phe Asn Ser Glu Lys Ala Arg Arg Glu Lys
                965                 970                 975
```

-continued

| | |
|---|---|
| tca ggc gct caa cac aat ggt cag cac tct att ggt ttg tta gat ttt<br>Ser Gly Ala Gln His Asn Gly Gln His Ser Ile Gly Leu Leu Asp Phe<br>      980                    985                    990 | 2976 |
| gca ttg att agc cta att atg gat aat gag ctc ttt gca gag acc ttt<br>Ala Leu Ile Ser Leu Ile Met Asp Asn Glu Leu Phe Ala Glu Thr Phe<br>    995                      1000                   1005 | 3024 |
| ttt aac aac tac aaa agt ttt acg acg acg ttg tgc gta ctg gaa aac<br>Phe Asn Asn Tyr Lys Ser Phe Thr Thr Thr Leu Cys Val Leu Glu Asn<br>      1010                   1015                 1020 | 3072 |
| ttg gca aag aga ttt atc ggt gcg aaa tcc tca gcc ata tct att agt<br>Leu Ala Lys Arg Phe Ile Gly Ala Lys Ser Ser Ala Ile Ser Ile Ser<br>1025                 1030                 1035                 1040 | 3120 |
| cta atc aat aag tta cgg aat tct gaa tca tcc cgg cag ata cca cct<br>Leu Ile Asn Lys Leu Arg Asn Ser Glu Ser Ser Arg Gln Ile Pro Pro<br>                1045                 1050                1055 | 3168 |
| tct act acc tcc aac cag ttt tca gcg agt ggc atc ttt aag cca tca<br>Ser Thr Thr Ser Asn Gln Phe Ser Ala Ser Gly Ile Phe Lys Pro Ser<br>            1060                 1065                 1070 | 3216 |
| tat gat gag ctt aaa ttc cct gtc tgg gat ctt aag gtc acc agc gtc<br>Tyr Asp Glu Leu Lys Phe Pro Val Trp Asp Leu Lys Val Thr Ser Val<br>        1075                 1080                 1085 | 3264 |
| gaa ggc tgt ccg cta gac tac ctt gca aag att cag atc gga gta ttg<br>Glu Gly Cys Pro Leu Asp Tyr Leu Ala Lys Ile Gln Ile Gly Val Leu<br>1090                 1095                 1100 | 3312 |
| gaa tca cta tac cat ttg att aga gag cat tat gcg gac ttc acc gat<br>Glu Ser Leu Tyr His Leu Ile Arg Glu His Tyr Ala Asp Phe Thr Asp<br>1105                 1110                 1115                 1120 | 3360 |
| gat ctc gct aac aac aaa acc ttt ctg gat att ctg aag atc att aac<br>Asp Leu Ala Asn Asn Lys Thr Phe Leu Asp Ile Leu Lys Ile Ile Asn<br>                1125                 1130                1135 | 3408 |
| cag gag gtt tat gat gag tgg gac aaa aga tta gat gac cta agg aat<br>Gln Glu Val Tyr Asp Glu Trp Asp Lys Arg Leu Asp Asp Leu Arg Asn<br>            1140                 1145                1150 | 3456 |
| aat aat aac agt agc cag aag agg aag aac agt tgc gat gat aat tct<br>Asn Asn Asn Ser Ser Gln Lys Arg Lys Asn Ser Cys Asp Asp Asn Ser<br>        1155                 1160                 1165 | 3504 |
| agt gcc aag att act ttc cat gtt aat gat gct cga cct gaa aac tcc<br>Ser Ala Lys Ile Thr Phe His Val Asn Asp Ala Arg Pro Glu Asn Ser<br>    1170                      1175                 1180 | 3552 |
| aat gag aat aag cgg ggt gcg gcg acg aat ttg ggg gat agc tcc tta<br>Asn Glu Asn Lys Arg Gly Ala Ala Thr Asn Leu Gly Asp Ser Ser Leu<br>1185                 1190                 1195                 1200 | 3600 |
| gca gca ttg gaa aaa ctt caa tgt aca tta cag gat cta tac gtg aag<br>Ala Ala Leu Glu Lys Leu Gln Cys Thr Leu Gln Asp Leu Tyr Val Lys<br>            1205                 1210                1215 | 3648 |
| att aag tcc tca tat caa cgc caa tta tat cgt cca ttg ggc gtc aca<br>Ile Lys Ser Ser Tyr Gln Arg Gln Leu Tyr Arg Pro Leu Gly Val Thr<br>        1220                 1225                 1230 | 3696 |
| aga aat tgc agg aaa gtt cac gat atg ctg tgc caa ttt cag ccg cag<br>Arg Asn Cys Arg Lys Val His Asp Met Leu Cys Gln Phe Gln Pro Gln<br>    1235                      1240                 1245 | 3744 |
| act agt atg tcc gct ctt atc atg aat gga tct agt gac aca ctt gat<br>Thr Ser Met Ser Ala Leu Ile Met Asn Gly Ser Ser Asp Thr Leu Asp<br>1250                 1255                 1260 | 3792 |
| aag atg gtt acc gaa ttc cag gcc ctg aaa cac acc gat tat gat gat<br>Lys Met Val Thr Glu Phe Gln Ala Leu Lys His Thr Asp Tyr Asp Asp<br>1265                 1270                 1275                 1280 | 3840 |
| att att aat tgg att tac aaa tta gat cat ttt att acc tcg aaa cta<br>Ile Ile Asn Trp Ile Tyr Lys Leu Asp His Phe Ile Thr Ser Lys Leu<br>            1285                 1290                1295 | 3888 |

```
aag ctt gtt tcg aac caa gac tgg att caa gtg tcg caa att tta gag    3936
Lys Leu Val Ser Asn Gln Asp Trp Ile Gln Val Ser Gln Ile Leu Glu
        1300                1305                1310 tct ttg tcg aat gat tct ctt gtt gct ttg ttc aat tat cca ttg cat    3984
Ser Leu Ser Asn Asp Ser Leu Val Ala Leu Phe Asn Tyr Pro Leu His
        1315                1320                1325 gcg gaa tct aat aat gta att gca agt gga agt tct cag ttg gat gat    4032
Ala Glu Ser Asn Asn Val Ile Ala Ser Gly Ser Ser Gln Leu Asp Asp
        1330                1335                1340 ctt caa att ttg gat ata ttc acc tgg tta tca acg ctt gag agt ggt    4080
Leu Gln Ile Leu Asp Ile Phe Thr Trp Leu Ser Thr Leu Glu Ser Gly
1345                1350                1355                1360 tca gca cac att att gat aag ttc cct gct agc gtt cag ttg ata gtc    4128
Ser Ala His Ile Ile Asp Lys Phe Pro Ala Ser Val Gln Leu Ile Val
        1365                1370                1375 aga ctg cat ttg tct ctg act aaa ttt ttt act gtg cat att gcc cat    4176
Arg Leu His Leu Ser Leu Thr Lys Phe Phe Thr Val His Ile Ala His
        1380                1385                1390 ctg cat tct acc tat gag gcc aga gtt aat act tgt tca ctt atc ttg    4224
Leu His Ser Thr Tyr Glu Ala Arg Val Asn Thr Cys Ser Leu Ile Leu
        1395                1400                1405 gag ata ctc aac ttt gtt cat gtt aag aat gcc aat gtt aat tta ttc    4272
Glu Ile Leu Asn Phe Val His Val Lys Asn Ala Asn Val Asn Leu Phe
        1410                1415                1420 cat tct gat gat gct ggg gag ggt tct atg gcc aca att tcg cca cat    4320
His Ser Asp Asp Ala Gly Glu Gly Ser Met Ala Thr Ile Ser Pro His
1425                1430                1435                1440 gtc cca tct ttc atc gaa aca gcc ata gaa aac gcc atc ata agt cca    4368
Val Pro Ser Phe Ile Glu Thr Ala Ile Glu Asn Ala Ile Ile Ser Pro
        1445                1450                1455 gaa tcc cga ttt ttt gag gtt tca tgg aag caa gcc tat aag aca ata    4416
Glu Ser Arg Phe Phe Glu Val Ser Trp Lys Gln Ala Tyr Lys Thr Ile
        1460                1465                1470 tcc gag aaa gat gag aag ttg acg ttc att gga tct gtg ctt acc ggg    4464
Ser Glu Lys Asp Glu Lys Leu Thr Phe Ile Gly Ser Val Leu Thr Gly
        1475                1480                1485 tta gat aaa tcg acg gcg cac ttt ttg gat gcc gat aac agg cag cct    4512
Leu Asp Lys Ser Thr Ala His Phe Leu Asp Ala Asp Asn Arg Gln Pro
        1490                1495                1500 gtt agg ccc aag aat ttt tcg cct tgc ccg ggt tgg ttt atc tct cgt    4560
Val Arg Pro Lys Asn Phe Ser Pro Cys Pro Gly Trp Phe Ile Ser Arg
1505                1510                1515                1520 ctg ttg gag atc act ggc cta gtt cct aac atg agc att gaa aat tcc    4608
Leu Leu Glu Ile Thr Gly Leu Val Pro Asn Met Ser Ile Glu Asn Ser
        1525                1530                1535 aaa atg atc aac ttt gac aaa agg cga ttc atc aat aac ata gtg ata    4656
Lys Met Ile Asn Phe Asp Lys Arg Arg Phe Ile Asn Asn Ile Val Ile
        1540                1545                1550 aac tat caa gac ttg att cca aat act gaa cag ctt ccg tct cat gat    4704
Asn Tyr Gln Asp Leu Ile Pro Asn Thr Glu Gln Leu Pro Ser His Asp
        1555                1560                1565 gat gaa aaa tcc gca cat caa ttt ggg tct atc ctt ttc cat tat ggc    4752
Asp Glu Lys Ser Ala His Gln Phe Gly Ser Ile Leu Phe His Tyr Gly
        1570                1575                1580 acc gag tca tcg att aag gca ttt aga aaa gct agt aag gag gct gct    4800
Thr Glu Ser Ser Ile Lys Ala Phe Arg Lys Ala Ser Lys Glu Ala Ala
1585                1590                1595                1600 tca aat gag gca aga aaa ttg aag ttt caa gca atg ggc ttg ttc aat    4848
Ser Asn Glu Ala Arg Lys Leu Lys Phe Gln Ala Met Gly Leu Phe Asn
```

-continued

| | | | |
|---|---|---|---|
| | 1605 | 1610 | 1615 |
| gat atc cta gtc act gaa gtc tac aag gtg cag aga gat caa aag aaa<br>Asp Ile Leu Val Thr Glu Val Tyr Lys Val Gln Arg Asp Gln Lys Lys<br>            1620                1625                1630 | | | 4896 |
| cag gaa cag tta acc gta cag gaa cat gag gca aaa aga tca gtc ttg<br>Gln Glu Gln Leu Thr Val Gln Glu His Glu Ala Lys Arg Ser Val Leu<br>1635                1640                1645 | | | 4944 |
| att caa cac cca aac aaa gtg tct gtc tct tcg gct tca tct tca gtc<br>Ile Gln His Pro Asn Lys Val Ser Val Ser Ser Ala Ser Ser Ser Val<br>            1650                1655                1660 | | | 4992 |
| tct ggg tct tcc agt ggc tct act gct aga act tct aat cct gct cat<br>Ser Gly Ser Ser Ser Gly Ser Thr Ala Arg Thr Ser Asn Pro Ala His<br>1665                1670                1675                1680 | | | 5040 |
| gct gct tac gcg tta aat atg gcc ggg tcc tta tca att tca gct gcc<br>Ala Ala Tyr Ala Leu Asn Met Ala Gly Ser Leu Ser Ile Ser Ala Ala<br>            1685                1690                1695 | | | 5088 |
| aga cat ggt aga agc tct gtt tca tct agg agt tcg gta ata tca aat<br>Arg His Gly Arg Ser Ser Val Ser Ser Arg Ser Ser Val Ile Ser Asn<br>            1700                1705                1710 | | | 5136 |
| acc gca act gct act tcc cca gca agt ggc gct tcc cca aac caa acc<br>Thr Ala Thr Ala Thr Ser Pro Ala Ser Gly Ala Ser Pro Asn Gln Thr<br>            1715                1720                1725 | | | 5184 |
| agc acc tct cat cat ggg ggc atg ggt aaa aaa att ggt ggc ttt ttg<br>Ser Thr Ser His His Gly Gly Met Gly Lys Lys Ile Gly Gly Phe Leu<br>1730                1735                1740 | | | 5232 |
| agg agg cca ttc tcc atc agt gga ttt acc tcg tca tcc tct caa tat<br>Arg Arg Pro Phe Ser Ile Ser Gly Phe Thr Ser Ser Ser Ser Gln Tyr<br>1745                1750                1755                1760 | | | 5280 |
| acc aca acg tca gtt gtg ctg tct ggc gtc cag gct aac ggc tct ata<br>Thr Thr Thr Ser Val Val Leu Ser Gly Val Gln Ala Asn Gly Ser Ile<br>            1765                1770                1775 | | | 5328 |
| tcc cca tat gag cta ccc gaa ctc act tcc gaa ata caa gat aca aag<br>Ser Pro Tyr Glu Leu Pro Glu Leu Thr Ser Glu Ile Gln Asp Thr Lys<br>            1780                1785                1790 | | | 5376 |
| atc gtc act gtc atc aag act ttt gag atc aaa tcg tgc atc caa atc<br>Ile Val Thr Val Ile Lys Thr Phe Glu Ile Lys Ser Cys Ile Gln Ile<br>            1795                1800                1805 | | | 5424 |
| aac aac tac agg cag gat cct gat atg atg cat tgt ttt aag att gtt<br>Asn Asn Tyr Arg Gln Asp Pro Asp Met Met His Cys Phe Lys Ile Val<br>1810                1815                1820 | | | 5472 |
| atg gag gat ggt aca caa cat acc ctt caa tgt atg gac gac gct gat<br>Met Glu Asp Gly Thr Gln His Thr Leu Gln Cys Met Asp Asp Ala Asp<br>1825                1830                1835                1840 | | | 5520 |
| atg cat gaa tgg atg aag gcc att aca ctc tct aaa aga tac tcc ttc<br>Met His Glu Trp Met Lys Ala Ile Thr Leu Ser Lys Arg Tyr Ser Phe<br>            1845                1850                1855 | | | 5568 |
| cat tct aaa aga ttt aag ggt aaa aca tca aat aaa atc ttc ggt gta<br>His Ser Lys Arg Phe Lys Gly Lys Thr Ser Asn Lys Ile Phe Gly Val<br>            1860                1865                1870 | | | 5616 |
| ccg gta gaa gac gtt tgc gaa aga gaa gga gcg tta ata ccc aat att<br>Pro Val Glu Asp Val Cys Glu Arg Glu Gly Ala Leu Ile Pro Asn Ile<br>            1875                1880                1885 | | | 5664 |
| ata gtg aaa ttg ttg gat gaa atc gag ttg cgc ggg ctt gat gaa gtg<br>Ile Val Lys Leu Leu Asp Glu Ile Glu Leu Arg Gly Leu Asp Glu Val<br>1890                1895                1900 | | | 5712 |
| ggc cta tat agg gtg cct ggt tcc gtg ggc agc atc aat gca ctc aag<br>Gly Leu Tyr Arg Val Pro Gly Ser Val Gly Ser Ile Asn Ala Leu Lys<br>1905                1910                1915                1920 | | | 5760 |
| aat gca ttt gac gat gag ggg gct gtt cac aac act ttt acg ctg gaa | | | 5808 |

-continued

```
        Asn Ala Phe Asp Asp Glu Gly Ala Val His Asn Thr Phe Thr Leu Glu
                        1925                1930                1935 gat gac cgt tgg ttt gaa ata aat act att gcc ggg tgt ttt aaa cta          5856
Asp Asp Arg Trp Phe Glu Ile Asn Thr Ile Ala Gly Cys Phe Lys Leu
            1940                1945                1950 tac ctc agg gaa ctt cct gaa tct ttg ttc aca aat gaa aag gtg gac          5904
Tyr Leu Arg Glu Leu Pro Glu Ser Leu Phe Thr Asn Glu Lys Val Asp
        1955                1960                1965 gag ttc gtt aat atc atg acc gct tac aag aac cat gag gtt gat cta          5952
Glu Phe Val Asn Ile Met Thr Ala Tyr Lys Asn His Glu Val Asp Leu
    1970                1975                1980 tcc cag ttc cag aat ggt ata aag acg ctg ctg agt acc ttg cct gtt          6000
Ser Gln Phe Gln Asn Gly Ile Lys Thr Leu Leu Ser Thr Leu Pro Val
1985                1990                1995                2000 ttc aat tac cat att cta aaa cgg ctg ttc ttg cat ctc aac cgc gtt          6048
Phe Asn Tyr His Ile Leu Lys Arg Leu Phe Leu His Leu Asn Arg Val
                2005                2010                2015 cac cag cat gtt gag aat aac aga atg gat gct agc aac ttg gca att          6096
His Gln His Val Glu Asn Asn Arg Met Asp Ala Ser Asn Leu Ala Ile
            2020                2025                2030 gtg ttt tcg atg tct ttc atc aac caa gat gat ctt gcc agt acg atg          6144
Val Phe Ser Met Ser Phe Ile Asn Gln Asp Asp Leu Ala Ser Thr Met
        2035                2040                2045 ggg ccc act ttg ggt ttg ctg caa atg cta cta cag cat ctg att aga          6192
Gly Pro Thr Leu Gly Leu Leu Gln Met Leu Leu Gln His Leu Ile Arg
    2050                2055                2060 aac cca gag cat tac ttc acc tga                                          6216
Asn Pro Glu His Tyr Phe Thr
2065                2070

<210> SEQ ID NO 6
<211> LENGTH: 2071
<212> TYPE: PRT
<213> ORGANISM: Ashbya gossypii

<400> SEQUENCE: 6

Met Pro Leu Lys Trp Ala Ala Arg Asn Lys Lys Pro Pro Ser Ala Pro
1               5                   10                  15

Gln Ser Cys Ala Ser Lys Pro Ser Ser Ala Ser Gln Ser Ser Cys Val
            20                  25                  30

Asp Glu Arg Ile Ser Ala Thr Pro Arg Ser Ser Ile Ser Ser Asn Ser
        35                  40                  45

Ser Pro Asn Ser Lys Asn Asn Met Ser Arg His Ser His Ser Asn Gly
    50                  55                  60

Ser Val Tyr Ser Asp Glu Thr Thr Leu Lys Thr Ala Gln Thr His Tyr
65                  70                  75                  80

Thr Gln Gln Gly Gln Gln Ala Lys Pro Gln Gln His Thr Gln Gln Gln
                85                  90                  95

Gln Gln Gln Pro Gln Thr Pro Met Gln Leu Gln Val Pro Thr Gly Gln
            100                 105                 110

Ala His Lys Arg Thr Leu Thr Cys Glu Asp Met Lys Ala Gly Ala Arg
        115                 120                 125

Cys Glu Glu Gln Val Ser Pro Cys Ser Gln Pro Ala Gly Ser Pro Val
    130                 135                 140

Arg Arg Gly Gly Gly Leu Asn Gly Glu Thr Tyr Asp Gly Thr Val Phe
145                 150                 155                 160

Arg Leu Gly Trp Val Asn Lys Ala Gln Gly Ala Ala Pro Ala Arg Glu
                165                 170                 175
```

-continued

```
Gly Arg Tyr Ser His Gln Pro Thr Ala Ser Leu Ser Ser Ile Gly Ser
            180                 185                 190
Glu Arg Pro His Phe Thr Gly Gly Thr Ser Gly Tyr Gln Tyr Val
        195                 200                 205
Ala Thr Ala Tyr Arg Leu His Arg Ala Gln Leu Lys Gly Cys Ile Leu
        210                 215                 220
Asn Leu Tyr Lys Ser Gly Leu Thr Asn Val Lys Tyr Phe Asp Pro Ala
225                 230                 235                 240
Leu Glu Pro Ser Ala Ala Ala Leu Gln Met His Gln Glu Arg Gln Glu
                245                 250                 255
Met Pro Leu Leu Gln Pro Pro Leu Pro Ser Glu Ala Val Pro Ala Pro
            260                 265                 270
Ser Ile Leu Glu Ala Ser Met Glu Ser Gly Glu Leu Arg Leu Glu Tyr
        275                 280                 285
Leu Ser Glu Ala Tyr Pro His Pro Asp Leu Gln Leu Asp Lys Lys Asp
        290                 295                 300
Gly Lys Ile Leu Ser Gly Ser Leu Glu Ser Leu Cys His Ala Val Leu
305                 310                 315                 320
Phe Met Pro Thr Thr Asp Ala Lys Arg Val Thr Asp Ile Leu Leu Leu
                325                 330                 335
Leu Pro Leu Leu Asp Asp Phe Thr Arg Val Leu Asn Tyr Phe Asn Leu
            340                 345                 350
Phe Gly Lys Val Phe Ser Lys His His Pro Ala Gly Ala Ala Gly Ala
            355                 360                 365
Asp Asp Leu Asn Gln Asn Tyr Asn Ile Ser Asn Glu Thr Asp Arg Gln
        370                 375                 380
Leu Thr Leu Arg Leu Ala Thr Val Val Gln Thr Val Leu Asp Met Phe
385                 390                 395                 400
Pro Gly Phe Leu Leu Asp Asp Lys Ile Phe Gln Ser Leu Val Ile Leu
                405                 410                 415
Leu Asp Thr Ile Ser Phe His Asp Glu Asp Thr Ser Gln Glu Leu Lys
            420                 425                 430
Val Ala Ile Ala Glu Lys Gln Thr Val Leu Val Lys Leu Thr Gly Phe
        435                 440                 445
Ala Asn Glu Pro Ile Gln Ser Ala Lys Leu Asp Val Leu Ile Lys Val
450                 455                 460
Gln Ser Phe Leu Lys Leu Asp Thr Glu Lys Val Ala Asn Gln Ile His
465                 470                 475                 480
Lys Ile Asn Leu Thr Phe Asn Arg Val Trp Ser Pro Gln Ala Asp Tyr
                485                 490                 495
Ser Leu Leu Tyr Asp Ser Gln Tyr Thr Gln Lys His Val Glu Leu Asn
            500                 505                 510
Pro Leu Val Phe Phe Asn Asp Lys Asn Val Gln Tyr Leu Ser Arg Leu
        515                 520                 525
Met Val Ser His Ile Phe Cys Glu Glu Thr Gly Phe Thr Pro Lys Lys
        530                 535                 540
Arg Ala Glu Val Leu Thr Lys Trp Val Gln Leu Gly Cys Lys Phe Glu
545                 550                 555                 560
Arg Leu Gly Asp Met Val Ser Trp Leu Ala Ile Ala Thr Val Ile Cys
                565                 570                 575
Ser Ile Pro Val Leu Arg Leu Thr Arg Thr Trp Gln Tyr Val Pro Asp
            580                 585                 590
```

-continued

Ser Tyr Leu Lys Ile Ile Phe Lys Asp Trp Val Pro Thr Ile Val Gln
        595             600             605

Leu Asp Arg Arg Gln Met Ser Ser Lys Ser Met Asn Ser Val Phe Ile
610             615             620

Leu Ala Pro Pro Asn Leu Asn Asp Ala Phe Val Arg Asp Asn Val Ile
625             630             635             640

Pro Tyr Phe Gly Asp Leu Val Ile His Ser Asp Leu Pro Arg Asp
        645             650             655

Ser Lys Tyr Lys Tyr Leu Glu Lys Lys Ile Arg Arg Thr Lys Asn Ala
        660             665             670

Phe Tyr Lys Trp Gln Gln Arg Leu Asp Gln Ala Phe Ala Gln Asp Arg
        675             680             685

Asp Ser Ala Ser Ser Phe Thr Asp Ser Leu His Leu Asp Glu Glu Glu
        690             695             700

His Asp Val Ala Asp Phe Tyr Gln Tyr Trp Arg Phe His Met Asn Leu
705             710             715             720

Pro Pro Met Asn Ile Glu Thr Ile Met Glu Met Ser Leu Lys Met Glu
                725             730             735

Pro Pro Ser Ile Asn Gln Gln Thr Tyr Ser Lys Thr Tyr Ser Thr Arg
                740             745             750

Ser Ala Leu Ile Ser Gly Ala Tyr Leu Pro Thr Leu Phe Thr Thr Leu
        755             760             765

Leu Pro Ser Tyr Ser Leu Phe Pro Gln Glu Leu Leu Ile Ala Ala Ala
770             775             780

Ser Thr Pro Ser Thr Lys Asn Asn Ser Ser Gln Ala Ser Asn Arg
785             790             795             800

Ile Ser Gln Leu Ser Val Asn Ser Thr Pro His Ser Asn Ala Ser Ser
                805             810             815

Ser Ser Ala Ala Ser Ala Val Thr Gly Ile Asp Asn Ile Asp Val Pro
                820             825             830

Ile Thr Lys Glu Ile Ser Ser Lys Leu Ser Asn Lys Gln Val Leu Leu
        835             840             845

Lys Phe Ile Arg Asp Met Phe Asn Val Asp Ile Asn Val Phe His Ile
850             855             860

Ser Asp Asp Val Ile Phe Lys Ser Ile Arg Asp Tyr Glu Ala Lys Ser
865             870             875             880

Arg Pro Thr Ser Val Val Ile Glu Ser Pro Lys Arg Leu Ser Leu Leu
                885             890             895

Ser Ser Val Ser Pro Asp Val Ser Ala Val Ser Ser Ala Leu Glu Asn
                900             905             910

Leu Asp Leu Phe Lys Asn Phe Asn Ser Ser Ser Asp Asp Ile Ala Glu
        915             920             925

Phe Thr Val Gln Val Val Leu Lys Cys Ala Ser Leu Glu Lys Ile Phe
        930             935             940

Asp Ile Leu Val Leu Thr Ser Arg Val Phe Ser Asn Leu Val Thr Thr
945             950             955             960

Thr Asp Leu Val Ser Tyr Phe Asn Ser Glu Lys Ala Arg Arg Glu Lys
                965             970             975

Ser Gly Ala Gln His Asn Gly Gln His Ser Ile Gly Leu Leu Asp Phe
                980             985             990

Ala Leu Ile Ser Leu Ile Met Asp Asn Glu Leu Phe Ala Glu Thr Phe
        995             1000            1005

Phe Asn Asn Tyr Lys Ser Phe Thr Thr Thr Leu Cys Val Leu Glu Asn

-continued

```
        1010                1015                1020
Leu Ala Lys Arg Phe Ile Gly Ala Lys Ser Ser Ala Ile Ser Ile Ser
1025                1030                1035                1040

Leu Ile Asn Lys Leu Arg Asn Ser Glu Ser Ser Arg Gln Ile Pro Pro
                1045                1050                1055

Ser Thr Thr Ser Asn Gln Phe Ser Ala Ser Gly Ile Phe Lys Pro Ser
                1060                1065                1070

Tyr Asp Glu Leu Lys Phe Pro Val Trp Asp Leu Lys Val Thr Ser Val
            1075                1080                1085

Glu Gly Cys Pro Leu Asp Tyr Leu Ala Lys Ile Gln Ile Gly Val Leu
        1090                1095                1100

Glu Ser Leu Tyr His Leu Ile Arg Glu His Tyr Ala Asp Phe Thr Asp
1105                1110                1115                1120

Asp Leu Ala Asn Asn Lys Thr Phe Leu Asp Ile Leu Lys Ile Ile Asn
                1125                1130                1135

Gln Glu Val Tyr Asp Glu Trp Asp Lys Arg Leu Asp Asp Leu Arg Asn
                1140                1145                1150

Asn Asn Asn Ser Ser Gln Lys Arg Lys Asn Ser Cys Asp Asp Asn Ser
            1155                1160                1165

Ser Ala Lys Ile Thr Phe His Val Asn Asp Ala Arg Pro Glu Asn Ser
        1170                1175                1180

Asn Glu Asn Lys Arg Gly Ala Ala Thr Asn Leu Gly Asp Ser Ser Leu
1185                1190                1195                1200

Ala Ala Leu Glu Lys Leu Gln Cys Thr Leu Gln Asp Leu Tyr Val Lys
                1205                1210                1215

Ile Lys Ser Ser Tyr Gln Arg Gln Leu Tyr Arg Pro Leu Gly Val Thr
                1220                1225                1230

Arg Asn Cys Arg Lys Val His Asp Met Leu Cys Gln Phe Gln Pro Gln
            1235                1240                1245

Thr Ser Met Ser Ala Leu Ile Met Asn Gly Ser Ser Asp Thr Leu Asp
        1250                1255                1260

Lys Met Val Thr Glu Phe Gln Ala Leu Lys His Thr Asp Tyr Asp Asp
1265                1270                1275                1280

Ile Ile Asn Trp Ile Tyr Lys Leu Asp His Phe Ile Thr Ser Lys Leu
                1285                1290                1295

Lys Leu Val Ser Asn Gln Asp Trp Ile Gln Val Ser Gln Ile Leu Glu
                1300                1305                1310

Ser Leu Ser Asn Asp Ser Leu Val Ala Leu Phe Asn Tyr Pro Leu His
            1315                1320                1325

Ala Glu Ser Asn Asn Val Ile Ala Ser Gly Ser Ser Gln Leu Asp Asp
        1330                1335                1340

Leu Gln Ile Leu Asp Ile Phe Thr Trp Leu Ser Thr Leu Glu Ser Gly
1345                1350                1355                1360

Ser Ala His Ile Ile Asp Lys Phe Pro Ala Ser Val Gln Leu Ile Val
                1365                1370                1375

Arg Leu His Leu Ser Leu Thr Lys Phe Phe Thr Val His Ile Ala His
                1380                1385                1390

Leu His Ser Thr Tyr Glu Ala Arg Val Asn Thr Cys Ser Leu Ile Leu
            1395                1400                1405

Glu Ile Leu Asn Phe Val His Val Lys Asn Ala Asn Val Asn Leu Phe
        1410                1415                1420

His Ser Asp Asp Ala Gly Glu Gly Ser Met Ala Thr Ile Ser Pro His
1425                1430                1435                1440
```

-continued

```
Val Pro Ser Phe Ile Glu Thr Ala Ile Glu Asn Ala Ile Ile Ser Pro
                1445                1450                1455
Glu Ser Arg Phe Phe Glu Val Ser Trp Lys Gln Ala Tyr Lys Thr Ile
                1460                1465                1470
Ser Glu Lys Asp Glu Lys Leu Thr Phe Ile Gly Ser Val Leu Thr Gly
                1475                1480                1485
Leu Asp Lys Ser Thr Ala His Phe Leu Asp Ala Asp Asn Arg Gln Pro
                1490                1495                1500
Val Arg Pro Lys Asn Phe Ser Pro Cys Pro Gly Trp Phe Ile Ser Arg
1505                1510                1515                1520
Leu Leu Glu Ile Thr Gly Leu Val Pro Asn Met Ser Ile Glu Asn Ser
                1525                1530                1535
Lys Met Ile Asn Phe Asp Lys Arg Arg Phe Ile Asn Asn Ile Val Ile
                1540                1545                1550
Asn Tyr Gln Asp Leu Ile Pro Asn Thr Glu Gln Leu Pro Ser His Asp
                1555                1560                1565
Asp Glu Lys Ser Ala His Gln Phe Gly Ser Ile Leu Phe His Tyr Gly
                1570                1575                1580
Thr Glu Ser Ser Ile Lys Ala Phe Arg Lys Ala Ser Lys Glu Ala Ala
1585                1590                1595                1600
Ser Asn Glu Ala Arg Lys Leu Lys Phe Gln Ala Met Gly Leu Phe Asn
                1605                1610                1615
Asp Ile Leu Val Thr Glu Val Tyr Lys Val Gln Arg Asp Gln Lys Lys
                1620                1625                1630
Gln Glu Gln Leu Thr Val Gln Glu His Glu Ala Lys Arg Ser Val Leu
                1635                1640                1645
Ile Gln His Pro Asn Lys Val Ser Val Ser Ser Ala Ser Ser Ser Val
1650                1655                1660
Ser Gly Ser Ser Gly Ser Thr Ala Arg Thr Ser Asn Pro Ala His
1665                1670                1675                1680
Ala Ala Tyr Ala Leu Asn Met Ala Gly Ser Leu Ser Ile Ser Ala Ala
                1685                1690                1695
Arg His Gly Arg Ser Ser Val Ser Ser Arg Ser Ser Val Ile Ser Asn
                1700                1705                1710
Thr Ala Thr Ala Thr Ser Pro Ala Ser Gly Ala Ser Pro Asn Gln Thr
                1715                1720                1725
Ser Thr Ser His His Gly Gly Met Gly Lys Lys Ile Gly Gly Phe Leu
                1730                1735                1740
Arg Arg Pro Phe Ser Ile Ser Gly Phe Thr Ser Ser Ser Ser Gln Tyr
1745                1750                1755                1760
Thr Thr Thr Ser Val Val Leu Ser Gly Val Gln Ala Asn Gly Ser Ile
                1765                1770                1775
Ser Pro Tyr Glu Leu Pro Glu Leu Thr Ser Glu Ile Gln Asp Thr Lys
                1780                1785                1790
Ile Val Thr Val Ile Lys Thr Phe Glu Ile Lys Ser Cys Ile Gln Ile
                1795                1800                1805
Asn Asn Tyr Arg Gln Asp Pro Asp Met Met His Cys Phe Lys Ile Val
                1810                1815                1820
Met Glu Asp Gly Thr Gln His Thr Leu Gln Cys Met Asp Ala Asp
1825                1830                1835                1840
Met His Glu Trp Met Lys Ala Ile Thr Leu Ser Lys Arg Tyr Ser Phe
                1845                1850                1855
```

```
His Ser Lys Arg Phe Lys Gly Lys Thr Ser Asn Lys Ile Phe Gly Val
            1860                1865                1870

Pro Val Glu Asp Val Cys Glu Arg Glu Gly Ala Leu Ile Pro Asn Ile
            1875                1880                1885

Ile Val Lys Leu Leu Asp Glu Ile Glu Leu Arg Gly Leu Asp Glu Val
            1890                1895                1900

Gly Leu Tyr Arg Val Pro Gly Ser Val Gly Ser Ile Asn Ala Leu Lys
1905                1910                1915                1920

Asn Ala Phe Asp Asp Glu Gly Ala Val His Asn Thr Phe Thr Leu Glu
                1925                1930                1935

Asp Asp Arg Trp Phe Glu Ile Asn Thr Ile Ala Gly Cys Phe Lys Leu
            1940                1945                1950

Tyr Leu Arg Glu Leu Pro Glu Ser Leu Phe Thr Asn Glu Lys Val Asp
            1955                1960                1965

Glu Phe Val Asn Ile Met Thr Ala Tyr Lys Asn His Glu Val Asp Leu
            1970                1975                1980

Ser Gln Phe Gln Asn Gly Ile Lys Thr Leu Leu Ser Thr Leu Pro Val
1985                1990                1995                2000

Phe Asn Tyr His Ile Leu Lys Arg Leu Phe Leu His Leu Asn Arg Val
                2005                2010                2015

His Gln His Val Glu Asn Asn Arg Met Asp Ala Ser Asn Leu Ala Ile
                2020                2025                2030

Val Phe Ser Met Ser Phe Ile Asn Gln Asp Asp Leu Ala Ser Thr Met
            2035                2040                2045

Gly Pro Thr Leu Gly Leu Leu Gln Met Leu Leu Gln His Leu Ile Arg
            2050                2055                2060

Asn Pro Glu His Tyr Phe Thr
2065                2070

<210> SEQ ID NO 7
<211> LENGTH: 3042
<212> TYPE: DNA
<213> ORGANISM: Ashbya gossypii
<220> FEATURE:
<221> NAME/KEY: CDS
<222> LOCATION: (1)..(3042)

<400> SEQUENCE: 7 atg gga gac ggg tca gac gca gaa cgc agc ggg ggg aca agc tcg tcc      48
Met Gly Asp Gly Ser Asp Ala Glu Arg Ser Gly Gly Thr Ser Ser Ser
1               5                  10                  15 tca gca ttg gaa ctt ctt gcg cag tat gag cag cac att atg gag cgg      96
Ser Ala Leu Glu Leu Leu Ala Gln Tyr Glu Gln His Ile Met Glu Arg
                20                  25                  30 ggg agg acg ttg gag gcg att gaa ggg cac ggc ggg gag cgg ctg ggg     144
Gly Arg Thr Leu Glu Ala Ile Glu Gly His Gly Gly Glu Arg Leu Gly
            35                  40                  45 cca acg tac gag gag ctt gtg gag gag aac gtg cag ctc cgg cgg gag     192
Pro Thr Tyr Glu Glu Leu Val Glu Glu Asn Val Gln Leu Arg Arg Glu
        50                  55                  60 ctg cag ggg cag cgg gag gaa ata gaa cac ctc cgc aaa acg att tct     240
Leu Gln Gly Gln Arg Glu Glu Ile Glu His Leu Arg Lys Thr Ile Ser
65                  70                  75                  80 ctg ctt gcg tcg ggg cgg agc ggc gcg acg gtg gtc gag cag cag gtg     288
Leu Leu Ala Ser Gly Arg Ser Gly Ala Thr Val Val Glu Gln Gln Val
                85                  90                  95 cgt cct gag cct tcg ccg tcc gta cga gag ctg gcg ctg ccg ccg cgg     336
Arg Pro Glu Pro Ser Pro Ser Val Arg Glu Leu Ala Leu Pro Pro Arg
```

-continued

|     |     |     | 100 |     |     |     |     | 105 |     |     |     |     | 110 |     |     |      |
|-----|-----|-----|-----|-----|-----|-----|-----|-----|-----|-----|-----|-----|-----|-----|-----|------|
| tcc | gcg | gac | cgg | cga | aag | aac | acc | aaa | aac | ctg | agt | ctc | gcc | ccg | gtg | 384  |
| Ser | Ala | Asp | Arg | Arg | Lys | Asn | Thr | Lys | Asn | Leu | Ser | Leu | Ala | Pro | Val |      |
|     |     |     | 115 |     |     |     |     | 120 |     |     |     |     | 125 |     |     |      |

```
ggc cac gag gtg ccg tcg acc gac cgg ctg cgt gtc tcg ccg cag gag      432
Gly His Glu Val Pro Ser Thr Asp Arg Leu Arg Val Ser Pro Gln Glu
        130                 135                 140 gcc acg agc ggg gca cag cag gtg ccc ttg cta acc tct tcg aag tcc      480
Ala Thr Ser Gly Ala Gln Gln Val Pro Leu Leu Thr Ser Ser Lys Ser
145                 150                 155                 160 gcc gag att ctg gtg tcg aaa tct ccg gat gaa gac cgc cac ttg atg      528
Ala Glu Ile Leu Val Ser Lys Ser Pro Asp Glu Asp Arg His Leu Met
                165                 170                 175 tcg cct agg aag aca att tca cgg tcc agt tcg tca tat tcg aat acg      576
Ser Pro Arg Lys Thr Ile Ser Arg Ser Ser Ser Tyr Ser Asn Thr
        180                 185                 190 cta ggc agc cct gca act tcc gtt ctg tat aag aac tct cgg ata tca      624
Leu Gly Ser Pro Ala Thr Ser Val Leu Tyr Lys Asn Ser Arg Ile Ser
        195                 200                 205 att act tct ccg tgc aag tct aac tct acg agc aaa gct gcg tct gtg      672
Ile Thr Ser Pro Cys Lys Ser Asn Ser Thr Ser Lys Ala Ala Ser Val
        210                 215                 220 ttg agt cta cca gaa aat aac acg tcc acc gag aat gcg ccg cat tca      720
Leu Ser Leu Pro Glu Asn Asn Thr Ser Thr Glu Asn Ala Pro His Ser
225                 230                 235                 240 cca cac aga ata gac aac gaa ttg gac ttg ctc acc gtg gag cct caa      768
Pro His Arg Ile Asp Asn Glu Leu Asp Leu Leu Thr Val Glu Pro Gln
                245                 250                 255 gat gga agc agg tac gat aca gag aga gca ggt ggt ccg ggg cca ttg      816
Asp Gly Ser Arg Tyr Asp Thr Glu Arg Ala Gly Gly Pro Gly Pro Leu
        260                 265                 270 tcg cct gag agc ata gtg tac agt gat tcg gac ttg caa gag cat caa      864
Ser Pro Glu Ser Ile Val Tyr Ser Asp Ser Asp Leu Gln Glu His Gln
        275                 280                 285 cct tct gat ctg tca tct acc act agg acg gat tta ggc aaa ttc aga      912
Pro Ser Asp Leu Ser Ser Thr Thr Arg Thr Asp Leu Gly Lys Phe Arg
        290                 295                 300 gat atg gtg gat act acc ttc aat gca gaa gac aac cct acg ggt tca      960
Asp Met Val Asp Thr Thr Phe Asn Ala Glu Asp Asn Pro Thr Gly Ser
305                 310                 315                 320 cga gac aag gag act gga acg gaa atg gag atc gct acg cta caa aat     1008
Arg Asp Lys Glu Thr Gly Thr Glu Met Glu Ile Ala Thr Leu Gln Asn
                325                 330                 335 acg ccc agc aga caa cat gaa tcg agt ttg gta aca agt cca caa gct     1056
Thr Pro Ser Arg Gln His Glu Ser Ser Leu Val Thr Ser Pro Gln Ala
        340                 345                 350 tct agg tca tcg att aca acg cca gtc gtg gat cct act aat acg agc     1104
Ser Arg Ser Ser Ile Thr Thr Pro Val Val Asp Pro Thr Asn Thr Ser
        355                 360                 365 gaa cct tct tcg ctt tca gca gcg aag ttt gga agt atg tct acc gct     1152
Glu Pro Ser Ser Leu Ser Ala Ala Lys Phe Gly Ser Met Ser Thr Ala
        370                 375                 380 aca tcc tcg aac aaa agg tcc aag ggc atg ggc act cct tcc gtg gaa     1200
Thr Ser Ser Asn Lys Arg Ser Lys Gly Met Gly Thr Pro Ser Val Glu
385                 390                 395                 400 cat tca gca aag tca tac tcg cag cat tct ggt agc ccc cac tct aac     1248
His Ser Ala Lys Ser Tyr Ser Gln His Ser Gly Ser Pro His Ser Asn
                405                 410                 415 tct cac cag tcc aag aaa gca gat att ccc tta ttt gta cag cca gag     1296
```

```
                Ser His Gln Ser Lys Lys Ala Asp Ile Pro Leu Phe Val Gln Pro Glu
                            420                 425                 430 gag tta ggt acg atc agg att gag gtc att agt aca ttg tat cat gag       1344
Glu Leu Gly Thr Ile Arg Ile Glu Val Ile Ser Thr Leu Tyr His Glu
            435                 440                 445 cct gga aac gca gcc agc att ctc ttt agt gtt gtt gat aag aag tct       1392
Pro Gly Asn Ala Ala Ser Ile Leu Phe Ser Val Val Asp Lys Lys Ser
450                 455                 460 tcc aag gag atg ttc aaa ttt gct aaa act ttt acc cgc att gca gag       1440
Ser Lys Glu Met Phe Lys Phe Ala Lys Thr Phe Thr Arg Ile Ala Glu
465                 470                 475                 480 ttc gat acc ttt atc aga aac aat atg gaa tct tta gcc gtc ccc ccc       1488
Phe Asp Thr Phe Ile Arg Asn Asn Met Glu Ser Leu Ala Val Pro Pro
                485                 490                 495 ctt ccc gac aag cac atg ttt gct tcg aac gtg cca gta aag gta gac       1536
Leu Pro Asp Lys His Met Phe Ala Ser Asn Val Pro Val Lys Val Asp
            500                 505                 510 agt agg aga gaa aag ctt aat gac tac ttt gct agt ttg ttg tat cta       1584
Ser Arg Arg Glu Lys Leu Asn Asp Tyr Phe Ala Ser Leu Leu Tyr Leu
        515                 520                 525 tcc cca tta ccc ttt aat cca gca ttg aag tta gcg caa ttc att agc       1632
Ser Pro Leu Pro Phe Asn Pro Ala Leu Lys Leu Ala Gln Phe Ile Ser
530                 535                 540 aca gac cct gtt atg aac cct ata act ggc gaa ttt gct aaa gag ggc       1680
Thr Asp Pro Val Met Asn Pro Ile Thr Gly Glu Phe Ala Lys Glu Gly
545                 550                 555                 560 atg cta cta gtc cgt aaa tct aaa acc ttg ggt agt act act acg tgg       1728
Met Leu Leu Val Arg Lys Ser Lys Thr Leu Gly Ser Thr Thr Thr Trp
                565                 570                 575 cgt att agg tac tgc aca gtt gag ggc tct ata atg cat ctc cat gac       1776
Arg Ile Arg Tyr Cys Thr Val Glu Gly Ser Ile Met His Leu His Asp
            580                 585                 590 cat atg att gat act gat acg atc aaa ttg acg cat tct acg att gaa       1824
His Met Ile Asp Thr Asp Thr Ile Lys Leu Thr His Ser Thr Ile Glu
        595                 600                 605 ctt cag gca aac ctc ccg gat gat aag tat ggg acc aag aat gga ttc       1872
Leu Gln Ala Asn Leu Pro Asp Asp Lys Tyr Gly Thr Lys Asn Gly Phe
    610                 615                 620 ata ctt aat gaa cac aaa aag agt ggt ctt tca agc tct aca aag tac       1920
Ile Leu Asn Glu His Lys Lys Ser Gly Leu Ser Ser Ser Thr Lys Tyr
625                 630                 635                 640 tat ttt tgc gct gaa acg cca aaa gaa cgt gaa caa tgg ata agc gta       1968
Tyr Phe Cys Ala Glu Thr Pro Lys Glu Arg Glu Gln Trp Ile Ser Val
                645                 650                 655 ttg acc act ctc tgc gat ggc cca ggt ggt aca gca gcc att cca tcc       2016
Leu Thr Thr Leu Cys Asp Gly Pro Gly Gly Thr Ala Ala Ile Pro Ser
            660                 665                 670 att aat agc aag tct gaa gcg tct agt tta ttc gag caa aca agc att       2064
Ile Asn Ser Lys Ser Glu Ala Ser Ser Leu Phe Glu Gln Thr Ser Ile
        675                 680                 685 agc gac tct agt tat ctt gga cca att gct aat ctc gag gca atg gat       2112
Ser Asp Ser Ser Tyr Leu Gly Pro Ile Ala Asn Leu Glu Ala Met Asp
    690                 695                 700 gca act tct ccg aca aga cca aat gat cca aac ccg gtc tcc tta aca       2160
Ala Thr Ser Pro Thr Arg Pro Asn Asp Pro Asn Pro Val Ser Leu Thr
705                 710                 715                 720 tct gaa gaa gag aaa gag gtc aag aga cga cgt atg aag tca ttc ttc       2208
Ser Glu Glu Glu Lys Glu Val Lys Arg Arg Arg Met Lys Ser Phe Phe
                725                 730                 735
```

```
cct ttc aag aag tta gct act aca cct acc ccc tac gct gct gga aac      2256
Pro Phe Lys Lys Leu Ala Thr Thr Pro Thr Pro Tyr Ala Ala Gly Asn
        740                 745                 750 gac aat gct tct ata ttt tcg caa gat gat gat agc cct gtg aat gct      2304
Asp Asn Ala Ser Ile Phe Ser Gln Asp Asp Asp Ser Pro Val Asn Ala
    755                 760                 765 aca aat gaa agt ggt att tca aga tca ctc cag tcc atg aat tta caa      2352
Thr Asn Glu Ser Gly Ile Ser Arg Ser Leu Gln Ser Met Asn Leu Gln
770                 775                 780 gca cag tat aac gcg gta ttt gga gcg gac ttg aga tcc tgt tta caa      2400
Ala Gln Tyr Asn Ala Val Phe Gly Ala Asp Leu Arg Ser Cys Leu Gln
785                 790                 795                 800 cta agt tcg cat ccc tac cag gga aaa tat gaa ata cca agt gtt gta      2448
Leu Ser Ser His Pro Tyr Gln Gly Lys Tyr Glu Ile Pro Ser Val Val
            805                 810                 815 ttc cga acg cta gaa ttc ttg tac aaa aac cgc ggc att cag gaa gaa      2496
Phe Arg Thr Leu Glu Phe Leu Tyr Lys Asn Arg Gly Ile Gln Glu Glu
        820                 825                 830 ggt ata ttt agg tta agc gga tcc agt tct ctc ata aaa tct ttg cag      2544
Gly Ile Phe Arg Leu Ser Gly Ser Ser Ser Leu Ile Lys Ser Leu Gln
    835                 840                 845 gag caa ttt gac aaa gaa tat gac gtg gat ttg tgc aat tac aac gat      2592
Glu Gln Phe Asp Lys Glu Tyr Asp Val Asp Leu Cys Asn Tyr Asn Asp
850                 855                 860 aaa gtt tct gtc aca cca gga aac gaa aat cag ggc ggt ctc tac gtc      2640
Lys Val Ser Val Thr Pro Gly Asn Glu Asn Gln Gly Gly Leu Tyr Val
865                 870                 875                 880 gat gtg aat acc gtt tca ggt tta tta aaa cta tac cta aga aag ctt      2688
Asp Val Asn Thr Val Ser Gly Leu Leu Lys Leu Tyr Leu Arg Lys Leu
            885                 890                 895 cct cat atg atc ttt ggg gat gct gca tat atg gat ttt aag aga atc      2736
Pro His Met Ile Phe Gly Asp Ala Ala Tyr Met Asp Phe Lys Arg Ile
        900                 905                 910 gtg gaa aga aac gga gat gat agc aaa cta ata gca ctc gag ttc agg      2784
Val Glu Arg Asn Gly Asp Asp Ser Lys Leu Ile Ala Leu Glu Phe Arg
    915                 920                 925 gca ttg gtt aat tcc gga cga att gcc aaa gaa tat gtc gcc tta atg      2832
Ala Leu Val Asn Ser Gly Arg Ile Ala Lys Glu Tyr Val Ala Leu Met
930                 935                 940 tat gca ttg ttc gag tta ttg gtg aag atc acc gag aac agc aaa tat      2880
Tyr Ala Leu Phe Glu Leu Leu Val Lys Ile Thr Glu Asn Ser Lys Tyr
945                 950                 955                 960 aac aag atg aat ctg cgg aat ttg tgt atc gta ttt tcg cca acg ttg      2928
Asn Lys Met Asn Leu Arg Asn Leu Cys Ile Val Phe Ser Pro Thr Leu
            965                 970                 975 aac ata ccc gtg aat ata cta cat ccg ttt atc act gac ttt ggc tgt      2976
Asn Ile Pro Val Asn Ile Leu His Pro Phe Ile Thr Asp Phe Gly Cys
        980                 985                 990 ata ttc caa gat aag gcg ccg atg gag aac gga cca ccg gtc aac ata      3024
Ile Phe Gln Asp Lys Ala Pro Met Glu Asn Gly Pro Pro Val Asn Ile
    995                 1000                1005 cac atc ccg caa att tag                                              3042
His Ile Pro Gln Ile
        1010
```

<210> SEQ ID NO 8
<211> LENGTH: 1013
<212> TYPE: PRT
<213> ORGANISM: Ashbya gossypii

<400> SEQUENCE: 8

-continued

```
Met Gly Asp Gly Ser Asp Ala Glu Arg Ser Gly Thr Ser Ser Ser
  1               5                  10                 15

Ser Ala Leu Glu Leu Leu Ala Gln Tyr Glu Gln His Ile Met Glu Arg
         20                  25                  30

Gly Arg Thr Leu Glu Ala Ile Glu Gly His Gly Gly Glu Arg Leu Gly
         35                  40                  45

Pro Thr Tyr Glu Glu Leu Val Glu Glu Asn Val Gln Leu Arg Arg Glu
         50                  55                  60

Leu Gln Gly Gln Arg Glu Glu Ile Glu His Leu Arg Lys Thr Ile Ser
 65                  70                  75                  80

Leu Leu Ala Ser Gly Arg Ser Gly Ala Thr Val Val Glu Gln Gln Val
                 85                  90                  95

Arg Pro Glu Pro Ser Pro Ser Val Arg Glu Leu Ala Leu Pro Pro Arg
                100                 105                 110

Ser Ala Asp Arg Arg Lys Asn Thr Lys Asn Leu Ser Leu Ala Pro Val
                115                 120                 125

Gly His Glu Val Pro Ser Thr Asp Arg Leu Arg Val Ser Pro Gln Glu
        130                 135                 140

Ala Thr Ser Gly Ala Gln Gln Val Pro Leu Leu Thr Ser Ser Lys Ser
145                 150                 155                 160

Ala Glu Ile Leu Val Ser Lys Ser Pro Asp Glu Asp Arg His Leu Met
                165                 170                 175

Ser Pro Arg Lys Thr Ile Ser Arg Ser Ser Ser Tyr Ser Asn Thr
                180                 185                 190

Leu Gly Ser Pro Ala Thr Ser Val Leu Tyr Lys Asn Ser Arg Ile Ser
        195                 200                 205

Ile Thr Ser Pro Cys Lys Ser Asn Ser Thr Ser Lys Ala Ala Ser Val
        210                 215                 220

Leu Ser Leu Pro Glu Asn Asn Thr Ser Thr Glu Asn Ala Pro His Ser
225                 230                 235                 240

Pro His Arg Ile Asp Asn Glu Leu Asp Leu Leu Thr Val Glu Pro Gln
                245                 250                 255

Asp Gly Ser Arg Tyr Asp Thr Glu Arg Ala Gly Gly Pro Gly Pro Leu
        260                 265                 270

Ser Pro Glu Ser Ile Val Tyr Ser Asp Ser Asp Leu Gln Glu His Gln
        275                 280                 285

Pro Ser Asp Leu Ser Ser Thr Thr Arg Thr Asp Leu Gly Lys Phe Arg
        290                 295                 300

Asp Met Val Asp Thr Thr Phe Asn Ala Glu Asp Asn Pro Thr Gly Ser
305                 310                 315                 320

Arg Asp Lys Glu Thr Gly Thr Glu Met Glu Ile Ala Thr Leu Gln Asn
                325                 330                 335

Thr Pro Ser Arg Gln His Glu Ser Ser Leu Val Thr Ser Pro Gln Ala
        340                 345                 350

Ser Arg Ser Ser Ile Thr Thr Pro Val Val Asp Pro Thr Asn Thr Ser
        355                 360                 365

Glu Pro Ser Ser Leu Ser Ala Ala Lys Phe Gly Ser Met Ser Thr Ala
        370                 375                 380

Thr Ser Ser Asn Lys Arg Ser Lys Gly Met Gly Thr Pro Ser Val Glu
385                 390                 395                 400

His Ser Ala Lys Ser Tyr Ser Gln His Ser Gly Ser Pro His Ser Asn
                405                 410                 415
```

```
Ser His Gln Ser Lys Lys Ala Asp Ile Pro Leu Phe Val Gln Pro Glu
            420                 425                 430

Glu Leu Gly Thr Ile Arg Ile Glu Val Ile Ser Thr Leu Tyr His Glu
            435                 440                 445

Pro Gly Asn Ala Ala Ser Ile Leu Phe Ser Val Val Asp Lys Lys Ser
            450                 455                 460

Ser Lys Glu Met Phe Lys Phe Ala Lys Thr Phe Thr Arg Ile Ala Glu
465                 470                 475                 480

Phe Asp Thr Phe Ile Arg Asn Asn Met Glu Ser Leu Ala Val Pro Pro
                485                 490                 495

Leu Pro Asp Lys His Met Phe Ala Ser Asn Val Pro Val Lys Val Asp
            500                 505                 510

Ser Arg Arg Glu Lys Leu Asn Asp Tyr Phe Ala Ser Leu Leu Tyr Leu
            515                 520                 525

Ser Pro Leu Pro Phe Asn Pro Ala Leu Lys Leu Ala Gln Phe Ile Ser
            530                 535                 540

Thr Asp Pro Val Met Asn Pro Ile Thr Gly Glu Phe Ala Lys Glu Gly
545                 550                 555                 560

Met Leu Leu Val Arg Lys Ser Lys Thr Leu Gly Ser Thr Thr Thr Trp
                565                 570                 575

Arg Ile Arg Tyr Cys Thr Val Glu Gly Ser Ile Met His Leu His Asp
                580                 585                 590

His Met Ile Asp Thr Asp Thr Ile Lys Leu Thr His Ser Thr Ile Glu
            595                 600                 605

Leu Gln Ala Asn Leu Pro Asp Asp Lys Tyr Gly Thr Lys Asn Gly Phe
            610                 615                 620

Ile Leu Asn Glu His Lys Lys Ser Gly Leu Ser Ser Ser Thr Lys Tyr
625                 630                 635                 640

Tyr Phe Cys Ala Glu Thr Pro Lys Glu Arg Glu Gln Trp Ile Ser Val
                645                 650                 655

Leu Thr Thr Leu Cys Asp Gly Pro Gly Gly Thr Ala Ala Ile Pro Ser
                660                 665                 670

Ile Asn Ser Lys Ser Glu Ala Ser Ser Leu Phe Glu Gln Thr Ser Ile
            675                 680                 685

Ser Asp Ser Ser Tyr Leu Gly Pro Ile Ala Asn Leu Glu Ala Met Asp
            690                 695                 700

Ala Thr Ser Pro Thr Arg Pro Asn Asp Pro Asn Pro Val Ser Leu Thr
705                 710                 715                 720

Ser Glu Glu Glu Lys Glu Val Lys Arg Arg Met Lys Ser Phe Phe
                725                 730                 735

Pro Phe Lys Lys Leu Ala Thr Thr Pro Thr Pro Tyr Ala Ala Gly Asn
                740                 745                 750

Asp Asn Ala Ser Ile Phe Ser Gln Asp Asp Ser Pro Val Asn Ala
            755                 760                 765

Thr Asn Glu Ser Gly Ile Ser Arg Ser Leu Gln Ser Met Asn Leu Gln
770                 775                 780

Ala Gln Tyr Asn Ala Val Phe Gly Ala Asp Leu Arg Ser Cys Leu Gln
785                 790                 795                 800

Leu Ser Ser His Pro Tyr Gln Gly Lys Tyr Glu Ile Pro Ser Val Val
                805                 810                 815

Phe Arg Thr Leu Glu Phe Leu Tyr Lys Asn Arg Gly Ile Gln Glu Glu
            820                 825                 830

Gly Ile Phe Arg Leu Ser Gly Ser Ser Ser Leu Ile Lys Ser Leu Gln
```

```
            835                 840                 845
Glu Gln Phe Asp Lys Glu Tyr Asp Val Asp Leu Cys Asn Tyr Asn Asp
        850                 855                 860

Lys Val Ser Val Thr Pro Gly Asn Glu Asn Gln Gly Gly Leu Tyr Val
865                 870                 875                 880

Asp Val Asn Thr Val Ser Gly Leu Leu Lys Leu Tyr Leu Arg Lys Leu
                885                 890                 895

Pro His Met Ile Phe Gly Asp Ala Ala Tyr Met Asp Phe Lys Arg Ile
            900                 905                 910

Val Glu Arg Asn Gly Asp Asp Ser Lys Leu Ile Ala Leu Glu Phe Arg
        915                 920                 925

Ala Leu Val Asn Ser Gly Arg Ile Ala Lys Glu Tyr Val Ala Leu Met
    930                 935                 940

Tyr Ala Leu Phe Glu Leu Leu Val Lys Ile Thr Glu Asn Ser Lys Tyr
945                 950                 955                 960

Asn Lys Met Asn Leu Arg Asn Leu Cys Ile Val Phe Ser Pro Thr Leu
                965                 970                 975

Asn Ile Pro Val Asn Ile Leu His Pro Phe Ile Thr Asp Phe Gly Cys
            980                 985                 990

Ile Phe Gln Asp Lys Ala Pro Met Glu Asn Gly Pro Pro Val Asn Ile
        995                 1000                1005

His Ile Pro Gln Ile
    1010

<210> SEQ ID NO 9
<211> LENGTH: 530
<212> TYPE: DNA
<213> ORGANISM: Ashbya gossypii
<220> FEATURE:
<221> NAME/KEY: CDS
<222> LOCATION: (1)..(528)

<400> SEQUENCE: 9 cag gcc atg cat gaa ggg tta aat ata ata aaa att gac aac tgg cta      48
Gln Ala Met His Glu Gly Leu Asn Ile Ile Lys Ile Asp Asn Trp Leu
  1               5                  10                  15 gaa gtg ata ccg cag ttg ata tcc cga att cac cag cct aac caa acc      96
Glu Val Ile Pro Gln Leu Ile Ser Arg Ile His Gln Pro Asn Gln Thr
             20                  25                  30 gtg agt aga aca tta tta tct ctc tta tct gac ctc ggc aag gct cat     144
Val Ser Arg Thr Leu Leu Ser Leu Leu Ser Asp Leu Gly Lys Ala His
         35                  40                  45 cct cag gct ctc gtc ttc cct cta aca gtt gct ata aaa tct gaa tct     192
Pro Gln Ala Leu Val Phe Pro Leu Thr Val Ala Ile Lys Ser Glu Ser
     50                  55                  60 gta tct agg cag aga gct gct ttg tct att atg gag aag atg cgt atg     240
Val Ser Arg Gln Arg Ala Ala Leu Ser Ile Met Glu Lys Met Arg Met
 65                  70                  75                  80 cat agt tct aat ctg gtt gaa cag gca gaa ctg gtt agc aat gag ctc     288
His Ser Ser Asn Leu Val Glu Gln Ala Glu Leu Val Ser Asn Glu Leu
                 85                  90                  95 att cgt att gct gtg ctg tgg cat gag cta tgg tat gaa ggt ctg gag     336
Ile Arg Ile Ala Val Leu Trp His Glu Leu Trp Tyr Glu Gly Leu Glu
            100                 105                 110 gac gcg agt aga cag ttt ctc gga gag cat aat acg gaa aag atg ttc     384
Asp Ala Ser Arg Gln Phe Leu Gly Glu His Asn Thr Glu Lys Met Phe
        115                 120                 125 gct act ttg gaa cca ctg cat gaa atg ttg aag agg gga cct gag act     432
```

-continued

```
Ala Thr Leu Glu Pro Leu His Glu Met Leu Lys Arg Gly Pro Glu Thr
            130                 135                 140 cta cgg gag ata tca ttc cag aat tca ttt ggt aga gac ctg aat gac       480
Leu Arg Glu Ile Ser Phe Gln Asn Ser Phe Gly Arg Asp Leu Asn Asp
145                 150                 155                 160 gca tat gaa tgg gtc atg aac tat aag agg aca cag gat atc agt aat       528
Ala Tyr Glu Trp Val Met Asn Tyr Lys Arg Thr Gln Asp Ile Ser Asn
                165                 170                 175 tt                                                                    530
```

<210> SEQ ID NO 10
<211> LENGTH: 176
<212> TYPE: PRT
<213> ORGANISM: Ashbya gossypii

<400> SEQUENCE: 10

```
Gln Ala Met His Glu Gly Leu Asn Ile Ile Lys Ile Asp Asn Trp Leu
  1               5                  10                  15

Glu Val Ile Pro Gln Leu Ile Ser Arg Ile His Gln Pro Asn Gln Thr
             20                  25                  30

Val Ser Arg Thr Leu Leu Ser Leu Leu Ser Asp Leu Gly Lys Ala His
         35                  40                  45

Pro Gln Ala Leu Val Phe Pro Leu Thr Val Ala Ile Lys Ser Glu Ser
     50                  55                  60

Val Ser Arg Gln Arg Ala Ala Leu Ser Ile Met Glu Lys Met Arg Met
 65                  70                  75                  80

His Ser Ser Asn Leu Val Glu Gln Ala Glu Leu Val Ser Asn Glu Leu
                 85                  90                  95

Ile Arg Ile Ala Val Leu Trp His Glu Leu Trp Tyr Glu Gly Leu Glu
            100                 105                 110

Asp Ala Ser Arg Gln Phe Leu Gly Glu His Asn Thr Glu Lys Met Phe
        115                 120                 125

Ala Thr Leu Glu Pro Leu His Glu Met Leu Lys Arg Gly Pro Glu Thr
    130                 135                 140

Leu Arg Glu Ile Ser Phe Gln Asn Ser Phe Gly Arg Asp Leu Asn Asp
145                 150                 155                 160

Ala Tyr Glu Trp Val Met Asn Tyr Lys Arg Thr Gln Asp Ile Ser Asn
                165                 170                 175
```

<210> SEQ ID NO 11
<211> LENGTH: 402
<212> TYPE: DNA
<213> ORGANISM: Ashbya gossypii
<220> FEATURE:
<221> NAME/KEY: CDS
<222> LOCATION: (1)..(402)

<400> SEQUENCE: 11

```
gtg gac act tca ggc atg tcg aga gag acg cta cgg tac tac gaa ttt        48
Val Asp Thr Ser Gly Met Ser Arg Glu Thr Leu Arg Tyr Tyr Glu Phe
  1               5                  10                  15 ctc tgt aga gtt gga gag gca aaa cgt tgg att gag gat gtg atc ggc        96
Leu Cys Arg Val Gly Glu Ala Lys Arg Trp Ile Glu Asp Val Ile Gly
             20                  25                  30 gag acg ata cct gga gaa ctc gag ttg gca gct ggt aat tca atg cgc       144
Glu Thr Ile Pro Gly Glu Leu Glu Leu Ala Ala Gly Asn Ser Met Arg
         35                  40                  45 gac ggc tat ttt ttg gcg aag gtc act caa acg att aaa cct gat ctt       192
Asp Gly Tyr Phe Leu Ala Lys Val Thr Gln Thr Ile Lys Pro Asp Leu
```

```
                50                   55                   60
gca cct aca att gta cct cct ggt cgg ttg cag ttc aag cat aca cag      240
Ala Pro Thr Ile Val Pro Pro Gly Arg Leu Gln Phe Lys His Thr Gln
 65                  70                  75                  80 aat att aat gct ttt ttt tcg ctg atg gat ttg gta ggc gta ccg gac      288
Asn Ile Asn Ala Phe Phe Ser Leu Met Asp Leu Val Gly Val Pro Asp
                 85                  90                  95 cta ttt cga ttt gaa ctg acc gac cta tac gag aag aaa gac gtt cca      336
Leu Phe Arg Phe Glu Leu Thr Asp Leu Tyr Glu Lys Lys Asp Val Pro
            100                 105                 110 aaa gtt ttt gag act tta cat gca gtc gcg aac att ctc aat agt agg      384
Lys Val Phe Glu Thr Leu His Ala Val Ala Asn Ile Leu Asn Ser Arg
        115                 120                 125 ttc ccc ggc gag att cct                                              402
Phe Pro Gly Glu Ile Pro
    130
```

<210> SEQ ID NO 12
<211> LENGTH: 134
<212> TYPE: PRT
<213> ORGANISM: Ashbya gossypii

<400> SEQUENCE: 12

```
Val Asp Thr Ser Gly Met Ser Arg Glu Thr Leu Arg Tyr Tyr Glu Phe
  1               5                  10                  15

Leu Cys Arg Val Gly Glu Ala Lys Arg Trp Ile Glu Asp Val Ile Gly
             20                  25                  30

Glu Thr Ile Pro Gly Glu Leu Glu Leu Ala Ala Gly Asn Ser Met Arg
         35                  40                  45

Asp Gly Tyr Phe Leu Ala Lys Val Thr Gln Thr Ile Lys Pro Asp Leu
     50                  55                  60

Ala Pro Thr Ile Val Pro Pro Gly Arg Leu Gln Phe Lys His Thr Gln
 65                  70                  75                  80

Asn Ile Asn Ala Phe Phe Ser Leu Met Asp Leu Val Gly Val Pro Asp
                 85                  90                  95

Leu Phe Arg Phe Glu Leu Thr Asp Leu Tyr Glu Lys Lys Asp Val Pro
            100                 105                 110

Lys Val Phe Glu Thr Leu His Ala Val Ala Asn Ile Leu Asn Ser Arg
        115                 120                 125

Phe Pro Gly Glu Ile Pro
    130
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 13
gctagggata acagggtaat                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 14

```
aggcatgcaa gcttagatct                                                     20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 15
gtttagtctg accatctcat ctg                                                 23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 16
tcgcagaccg ataccaggat c                                                   21

<210> SEQ ID NO 17
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 17
aggaccacta gctcgttgcg ctgcaatata ataataagaa cgagagctag ggataacagg         60
gtaat                                                                     65

<210> SEQ ID NO 18
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 18
aagtattcaa tcaactatgt gagtagtttc ttgtaggcag tctccaggca tgcaagctta         60
gatct                                                                     65

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 19
ctggcatcag aggaagctcc caccaccaag ctctacaaac acaaggctag ggataacagg         60
gtaat                                                                     65

<210> SEQ ID NO 20
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 20
attatattag tatagtctaa agttgcaggc agtgggtatt aaagtaggca tgcaagctta         60
```

```
gatct                                                              65

<210> SEQ ID NO 21
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 21
acttgcgtac tctttcgcgt gctcgtcagc caccgaacaa cgcaggctag ggataacagg    60
gtaat                                                              65

<210> SEQ ID NO 22
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 22
ttaaagaatg ataaagaacc aaaaacacca cgagcttgca taacaaggca tgcaagctta    60
gatct                                                              65

<210> SEQ ID NO 23
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 23
gtgcgtgtca gcgagcatct aatcaagctg caaggcgccg gaaatgctag ggataacagg    60
gtaat                                                              65

<210> SEQ ID NO 24
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 24
ttatcacata tttctaagtt aatagatatt tttacttagt atgaaaggca tgcaagctta    60
gatct                                                              65

<210> SEQ ID NO 25
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 25
gagagagacg ctacggtact acgaatttct ctgtagagtt ggagagctag ggataacagg    60
gtaat                                                              65

<210> SEQ ID NO 26
<211> LENGTH: 65
<212> TYPE: DNA
<213> ORGANISM: Artificial Sequence
<220> FEATURE:
```

-continued

```
<223> OTHER INFORMATION: Description of Artificial Sequence:Primer

<400> SEQUENCE: 26
tactattgag aatgttcgcg actgcatgta aagtctcaaa aacttaggca tgcaagctta      60
gatct                                                                 65

<210> SEQ ID NO 27
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 27
aaatataata aaaattgaca actggctaga agtgataccg cagttgctag ggataacagg      60
gtaat                                                                 65

<210> SEQ ID NO 28
<211> LENGTH: 65
<212> TYPE: DNA
<213> ORGANISM: Artificial Sequence
<220> FEATURE:
<223> OTHER INFORMATION: Description of Artificial Sequence:Primer

<400> SEQUENCE: 28
cctcttatag ttcatgaccc attcatatgc gtcattcagg tctctaggca tgcaagctta      60
gatct                                                                 65
```